(12) United States Patent
Gibson

(10) Patent No.: US 12,427,260 B2
(45) Date of Patent: Sep. 30, 2025

(54) INJECTOR AND METHOD OF ASSEMBLY

(71) Applicant: AMGEN INC., Thousand Oaks, CA (US)

(72) Inventor: Scott R. Gibson, Simi Valley, CA (US)

(73) Assignee: AMGEN INC., Thousand Oaks, CA (US)

( * ) Notice: Subject to any disclaimer, the term of this patent is extended or adjusted under 35 U.S.C. 154(b) by 228 days.

(21) Appl. No.: 17/380,749

(22) Filed: Jul. 20, 2021

(65) Prior Publication Data

US 2021/0361869 A1 Nov. 25, 2021

Related U.S. Application Data

(63) Continuation of application No. 14/916,208, filed as application No. PCT/US2014/061675 on Oct. 22, 2014, now Pat. No. 11,097,055.

(Continued)

(51) Int. Cl.
*A61M 5/24* (2006.01)
*A61M 5/178* (2006.01)
(Continued)

(52) U.S. Cl.
CPC ........ *A61M 5/2466* (2013.01); *A61M 5/1782* (2013.01); *A61M 5/288* (2013.01);
(Continued)

(58) Field of Classification Search
CPC ........ A61M 5/34; A61M 5/345; A61M 5/348; A61M 5/347
See application file for complete search history.

(56) References Cited

U.S. PATENT DOCUMENTS 2,371,086 A 3/1945 Watson et al.
2,591,706 A 4/1952 Lockhart
(Continued)

FOREIGN PATENT DOCUMENTS

AT 404556 B 12/1998
CA 2779793 A1 5/2011
(Continued)

OTHER PUBLICATIONS

Chinese Patent Application for Invention No. 201480058204.9, Office Action, dated Sep. 23, 2021.
(Continued)

*Primary Examiner* — William R Carpenter
(74) *Attorney, Agent, or Firm* — MARSHALL, GERSTEIN & BORUN LLP

(57) ABSTRACT

An injector may include a container having a wall with an interior surface defining a closed sterile reservoir filled with a medical fluid or drug product. The injector may also include a fluid delivery system comprising a sterile container needle that is in fluid communication with the container in a delivery state, but may or may not be in fluid communication with the container in a storage state. The sterile container needle is attached to a connector, the connector mechanically coupled to the container to secure the sterile container needle to the container with the needle in the storage state. Further, the injector may include an actuator that is adapted to move the container needle from the storage state to the delivery state.

18 Claims, 10 Drawing Sheets

Related U.S. Application Data

(60) Provisional application No. 61/895,390, filed on Oct. 24, 2013.

(51) Int. Cl.
*A61M 5/28* (2006.01)
*A61M 5/315* (2006.01)

(52) U.S. Cl.
CPC ....... *A61M 5/315* (2013.01); *A61M 2005/247* (2013.01); *A61M 2005/31588* (2013.01); *A61M 2202/04* (2013.01); *A61M 2207/00* (2013.01)

(56) References Cited

U.S. PATENT DOCUMENTS

| | | |
|---|---|---|
| 2,677,373 A | 5/1954 | Barradas |
| 2,688,967 A | 9/1954 | Huber |
| 2,842,126 A | 7/1958 | Brown |
| 3,187,749 A | 6/1965 | Sarnoff |
| 3,336,924 A * | 8/1967 | Sarnoff ............... A61J 1/2096 206/229 |
| 3,342,180 A | 9/1967 | Sandhage |
| 3,368,557 A | 2/1968 | Hassing et al. |
| 3,368,558 A | 2/1968 | Sarnoff et al. |
| 3,376,866 A | 4/1968 | Ogle |
| 3,557,787 A | 1/1971 | Cohen |
| 3,605,744 A * | 9/1971 | Dwyer ............... A61M 5/24 604/157 |
| 3,640,278 A | 2/1972 | Friedman |
| 3,662,753 A | 5/1972 | Tassell |
| 3,682,174 A | 8/1972 | Cohen |
| 3,739,779 A | 6/1973 | Pfleger |
| 3,739,947 A | 6/1973 | Baumann et al. |
| 3,757,779 A | 9/1973 | Rovinski |
| 3,785,379 A | 1/1974 | Cohen |
| 3,825,003 A | 7/1974 | Kruck |
| 3,835,855 A | 9/1974 | Barr, Jr. |
| 3,872,864 A | 3/1975 | Allen, Jr. |
| 3,872,867 A | 3/1975 | Killinger |
| 3,916,893 A | 11/1975 | De Felice |
| 3,967,621 A | 7/1976 | Schwarz |
| 3,995,630 A | 12/1976 | van de Veerdonk |
| 4,055,177 A | 10/1977 | Cohen |
| 4,178,930 A | 12/1979 | Fisher, Jr. |
| 4,188,949 A | 2/1980 | Antoshkiw |
| 4,196,732 A | 4/1980 | Wardlaw |
| 4,215,689 A | 8/1980 | Akiyama et al. |
| 4,281,653 A | 8/1981 | Barta et al. |
| 4,296,786 A | 10/1981 | Brignola |
| 4,411,163 A | 10/1983 | White |
| 4,523,679 A | 6/1985 | Paikoff et al. |
| 4,576,211 A | 3/1986 | Valentini et al. |
| 4,619,651 A * | 10/1986 | Kopfer ............... A61J 1/2096 604/87 |
| 4,626,244 A | 12/1986 | Reinicke |
| 4,632,672 A | 12/1986 | Kvitrud |
| 4,655,747 A | 4/1987 | Allen, Jr. |
| 4,753,638 A | 6/1988 | Peters |
| 4,784,156 A | 11/1988 | Garg |
| 4,834,714 A | 5/1989 | Lascar et al. |
| 4,838,857 A | 6/1989 | Strowe et al. |
| 4,883,473 A | 11/1989 | Thomas |
| 4,915,690 A | 4/1990 | Cone et al. |
| 4,919,658 A * | 4/1990 | Badia ............... A61M 5/162 604/199 |
| 4,927,019 A * | 5/1990 | Haber ............... A61M 5/3213 206/365 |
| 5,019,047 A | 5/1991 | Kriesel |
| 5,078,691 A | 1/1992 | Hamacher |
| 5,135,489 A | 8/1992 | Jepson et al. |
| 5,147,328 A | 9/1992 | Dragosits et al. |
| 5,205,820 A | 4/1993 | Kriesel |
| 5,267,974 A | 12/1993 | Lambert |
| 5,312,336 A | 5/1994 | Haber et al. |
| 5,334,197 A | 8/1994 | Kriesel et al. |
| 5,358,491 A | 10/1994 | Johnson et al. |
| 5,364,369 A | 11/1994 | Reynolds et al. |
| 5,441,490 A | 8/1995 | Svedman |
| 5,480,386 A | 1/1996 | Brohy et al. |
| 5,496,284 A | 3/1996 | Waldenburg |
| 5,593,391 A | 1/1997 | Stanners |
| 5,618,269 A | 4/1997 | Jacobsen et al. |
| 5,620,425 A | 4/1997 | Heffernan et al. |
| 5,643,206 A | 7/1997 | Fischer |
| 5,693,018 A | 12/1997 | Kriesel et al. |
| 5,713,866 A | 2/1998 | Wilmot |
| 5,749,857 A | 5/1998 | Cuppy |
| 5,807,323 A | 9/1998 | Kriesel et al. |
| 5,865,744 A | 2/1999 | Lemelson |
| 5,885,250 A | 3/1999 | Kriesel et al. |
| 5,921,962 A | 7/1999 | Kriesel et al. |
| 5,957,891 A | 9/1999 | Kriesel et al. |
| 5,957,895 A | 9/1999 | Sage et al. |
| 5,957,896 A | 9/1999 | Bendek et al. |
| 5,962,794 A | 10/1999 | Kriesel et al. |
| 6,027,482 A | 2/2000 | Imbert |
| 6,065,270 A | 5/2000 | Reinhard et al. |
| 6,068,613 A | 5/2000 | Kriesel et al. |
| 6,159,180 A | 12/2000 | Kriesel et al. |
| 6,189,292 B1 | 2/2001 | Odell et al. |
| 6,221,055 B1 | 4/2001 | Shaw et al. |
| 6,248,095 B1 | 6/2001 | Giambattista et al. |
| 6,355,019 B1 | 3/2002 | Kriesel et al. |
| 6,482,176 B1 | 11/2002 | Wich |
| 6,491,665 B1 | 12/2002 | Vetter et al. |
| 6,491,667 B1 | 12/2002 | Keane et al. |
| 6,537,249 B2 | 3/2003 | Kriesell et al. |
| 6,589,229 B1 | 7/2003 | Connelly et al. |
| 6,595,956 B1 | 7/2003 | Gross et al. |
| 6,793,646 B1 | 9/2004 | Giambattista et al. |
| 6,824,529 B2 | 11/2004 | Gross et al. |
| 6,883,222 B2 | 4/2005 | Landau |
| 7,033,343 B2 | 4/2006 | McWethy et al. |
| 7,063,684 B2 | 6/2006 | Moberg |
| 7,112,188 B2 | 9/2006 | Waldenburg |
| 7,169,132 B2 | 1/2007 | Bendek et al. |
| 7,220,245 B2 | 5/2007 | Kriesel |
| 7,250,037 B2 | 7/2007 | Shermer et al. |
| 7,402,150 B2 | 7/2008 | Matsumoto et al. |
| 7,475,797 B2 | 1/2009 | Kim |
| 7,524,300 B2 | 4/2009 | Patton |
| 7,608,055 B2 | 10/2009 | Griffiths et al. |
| 7,628,782 B2 | 12/2009 | Adair et al. |
| 7,641,649 B2 | 1/2010 | Moberg et al. |
| 7,686,787 B2 | 3/2010 | Moberg et al. |
| 7,704,228 B2 | 4/2010 | Patton |
| 7,731,680 B2 | 6/2010 | Patton |
| 7,744,589 B2 | 6/2010 | Mounce et al. |
| 7,749,190 B2 | 7/2010 | Griffiths et al. |
| 7,776,030 B2 | 8/2010 | Estes et al. |
| 7,789,853 B2 | 9/2010 | Kriesel |
| 7,789,857 B2 | 9/2010 | Moberg et al. |
| 7,828,772 B2 | 11/2010 | Kriesel et al. |
| 7,832,078 B2 | 11/2010 | Thilly et al. |
| 7,837,653 B2 | 11/2010 | Kriesel et al. |
| 7,879,026 B2 | 2/2011 | Estes et al. |
| 7,905,868 B2 | 3/2011 | Moberg et al. |
| 7,935,087 B2 | 5/2011 | Judd et al. |
| 7,935,105 B2 | 5/2011 | Miller et al. |
| 7,938,801 B2 | 5/2011 | Hawkins et al. |
| 7,955,305 B2 | 6/2011 | Moberg et al. |
| 7,963,956 B2 | 6/2011 | Kunst |
| 8,021,333 B2 | 9/2011 | Kaal et al. |
| 8,025,658 B2 | 9/2011 | Chong et al. |
| 8,029,468 B2 | 10/2011 | Kriesel et al. |
| 8,030,457 B2 | 10/2011 | Jackson et al. |
| 8,032,226 B2 | 10/2011 | Miller et al. |
| 8,062,253 B2 | 11/2011 | Nielsen et al. |
| 8,105,279 B2 | 1/2012 | Mernoe et al. |
| 8,142,398 B1 | 3/2012 | Kriesel |
| 8,177,775 B2 | 5/2012 | Kunst |
| 8,292,848 B2 | 10/2012 | Kriesel et al. |

(56) References Cited

U.S. PATENT DOCUMENTS

| | | | |
|---|---|---|---|
| 8,303,535 | B2 | 11/2012 | Both et al. |
| 8,328,449 | B2 | 12/2012 | Wightman et al. |
| 8,353,866 | B2 | 1/2013 | Evans, Jr. |
| 8,372,035 | B2 | 2/2013 | Matusch |
| 8,409,142 | B2 | 4/2013 | Causey et al. |
| 8,454,562 | B1 | 6/2013 | Sims |
| 8,568,367 | B2 | 10/2013 | Griffiths et al. |
| 8,597,256 | B2 | 12/2013 | Lanin et al. |
| 8,603,034 | B2 | 12/2013 | Lynch et al. |
| 8,647,302 | B2 | 2/2014 | Briones et al. |
| 8,684,968 | B2 | 4/2014 | Genosar |
| 8,728,024 | B2 | 5/2014 | Kamen et al. |
| 8,905,974 | B2 | 12/2014 | Carter et al. |
| 8,961,467 | B2 | 2/2015 | Lanigan et al. |
| 9,125,981 | B2 | 9/2015 | Mann et al. |
| 9,205,194 | B2 | 12/2015 | Mojdehbakhsh et al. |
| 9,987,428 | B2 | 6/2018 | Tan-Malecki et al. |
| 10,092,706 | B2* | 10/2018 | Denzer .................. A61M 5/20 |
| 10,314,976 | B2 | 6/2019 | Tan-Malecki et al. |
| 10,537,681 | B2 | 1/2020 | Tan-Malecki et al. |
| 10,537,682 | B2 | 1/2020 | Tan-Malecki et al. |
| 10,850,037 | B2 | 12/2020 | Gibson |
| 11,058,821 | B2 | 7/2021 | Tan-Malecki et al. |
| 11,097,055 | B2 | 8/2021 | Gibson |
| 11,110,225 | B2 | 9/2021 | Tan-Malecki et al. |
| 11,129,941 | B2 | 9/2021 | Tan-Malecki et al. |
| 11,160,931 | B2 | 11/2021 | Tan-Malecki et al. |
| 2002/0139088 | A1 | 10/2002 | Woodworth et al. |
| 2002/0173753 | A1 | 11/2002 | Caizza et al. |
| 2003/0055380 | A1 | 3/2003 | Flaherty |
| 2003/0132547 | A1 | 7/2003 | Heffernan et al. |
| 2003/0191291 | A1* | 10/2003 | Kochendoerfer ....... A61P 37/00 |
| | | | 530/397 |
| 2003/0212362 | A1 | 11/2003 | Roser |
| 2004/0010207 | A1 | 1/2004 | Flaherty et al. |
| 2004/0015135 | A1 | 1/2004 | Wilkinson |
| 2004/0074076 | A1 | 4/2004 | Landau |
| 2004/0092865 | A1 | 5/2004 | Flaherty et al. |
| 2004/0092878 | A1 | 5/2004 | Flaherty |
| 2004/0133159 | A1 | 7/2004 | Haider et al. |
| 2004/0236273 | A1 | 11/2004 | Tanaka et al. |
| 2005/0113763 | A1 | 5/2005 | Reynolds |
| 2005/0154357 | A1 | 7/2005 | Pinel |
| 2005/0177108 | A1 | 8/2005 | Paul et al. |
| 2005/0267422 | A1 | 12/2005 | Kriesel |
| 2005/0277883 | A1 | 12/2005 | Kriesel |
| 2006/0178644 | A1 | 8/2006 | Reynolds |
| 2006/0191594 | A1 | 8/2006 | Py |
| 2006/0217659 | A1 | 9/2006 | Patton |
| 2006/0264900 | A1 | 11/2006 | Patton |
| 2006/0264901 | A1 | 11/2006 | Patton |
| 2007/0049875 | A1 | 3/2007 | Patton |
| 2007/0060877 | A1 | 3/2007 | Bassarab et al. |
| 2007/0100294 | A1 | 5/2007 | Sugita et al. |
| 2007/0186510 | A1 | 8/2007 | Wittland et al. |
| 2007/0276338 | A1 | 11/2007 | Shue et al. |
| 2007/0282269 | A1 | 12/2007 | Carter et al. |
| 2008/0009835 | A1 | 1/2008 | Kriesel et al. |
| 2008/0051711 | A1 | 2/2008 | Mounce et al. |
| 2008/0097306 | A1 | 4/2008 | Smith et al. |
| 2008/0140019 | A1 | 6/2008 | Thilly et al. |
| 2008/0154243 | A1 | 6/2008 | Krumme |
| 2008/0172034 | A1 | 7/2008 | Patton |
| 2008/0183140 | A1 | 7/2008 | Paproski et al. |
| 2008/0215004 | A1 | 9/2008 | Harding et al. |
| 2008/0215035 | A1 | 9/2008 | Yodfat et al. |
| 2008/0243084 | A1 | 10/2008 | DeStefano et al. |
| 2008/0243085 | A1 | 10/2008 | DeStefano |
| 2008/0269681 | A1 | 10/2008 | Kavazov et al. |
| 2008/0319385 | A1 | 12/2008 | Kriesel et al. |
| 2009/0009290 | A1* | 1/2009 | Kneip .................. A61M 1/155 |
| | | | 340/10.1 |
| 2009/0024083 | A1 | 1/2009 | Kriesel et al. |
| 2009/0099522 | A1 | 4/2009 | Kamen et al. |
| 2009/0192471 | A1 | 7/2009 | Carter et al. |
| 2009/0259209 | A1 | 10/2009 | Chong et al. |
| 2009/0270811 | A1 | 10/2009 | Mounce et al. |
| 2009/0275888 | A1 | 11/2009 | Kriesel et al. |
| 2009/0299277 | A1 | 12/2009 | Kamen et al. |
| 2010/0010472 | A1 | 1/2010 | Moore |
| 2010/0047914 | A1 | 2/2010 | Peyman et al. |
| 2010/0049128 | A1 | 2/2010 | McKenzie et al. |
| 2010/0082010 | A1 | 4/2010 | Adair et al. |
| 2010/0140125 | A1 | 6/2010 | Mathiasen et al. |
| 2010/0173024 | A1 | 7/2010 | McDaniel |
| 2010/0179473 | A1 | 7/2010 | Genosar |
| 2010/0198182 | A1 | 8/2010 | Lanigan et al. |
| 2010/0198183 | A1 | 8/2010 | Lanigan et al. |
| 2010/0217242 | A1 | 8/2010 | Mann et al. |
| 2010/0239654 | A1 | 9/2010 | Winter |
| 2010/0249753 | A1 | 9/2010 | Gaisser et al. |
| 2010/0298811 | A1 | 11/2010 | Connair |
| 2011/0004188 | A1 | 1/2011 | Shekalim |
| 2011/0022002 | A1 | 1/2011 | Hanson et al. |
| 2011/0054390 | A1 | 3/2011 | Searle et al. |
| 2011/0092904 | A1 | 4/2011 | Kriesel et al. |
| 2011/0097318 | A1 | 4/2011 | Gadgil |
| 2011/0112484 | A1 | 5/2011 | Carter et al. |
| 2011/0112501 | A1 | 5/2011 | Garfield et al. |
| 2011/0112504 | A1 | 5/2011 | Causey et al. |
| 2011/0137294 | A1 | 6/2011 | Calimeri et al. |
| 2011/0160696 | A1 | 6/2011 | Hoss |
| 2011/0166512 | A1 | 7/2011 | Both et al. |
| 2011/0190694 | A1 | 8/2011 | Lanier, Jr. et al. |
| 2011/0202004 | A1 | 8/2011 | Miller et al. |
| 2011/0224640 | A1* | 9/2011 | Kuhn .................. B65D 51/002 |
| | | | 604/414 |
| 2011/0245773 | A1 | 10/2011 | Estes et al. |
| 2011/0282300 | A1 | 11/2011 | Kriesel et al. |
| 2012/0010594 | A1 | 1/2012 | Holt et al. |
| 2012/0022499 | A1 | 1/2012 | Anderson et al. |
| 2012/0029440 | A1 | 2/2012 | Boyd et al. |
| 2012/0083738 | A1 | 4/2012 | Grant et al. |
| 2012/0123384 | A1 | 5/2012 | Mernoe et al. |
| 2012/0130318 | A1* | 5/2012 | Young .................. A61M 5/2429 |
| | | | 604/191 |
| 2012/0143144 | A1 | 6/2012 | Young |
| 2012/0179109 | A1 | 7/2012 | Takemoto et al. |
| 2012/0191060 | A1 | 7/2012 | Banister et al. |
| 2012/0191074 | A1 | 7/2012 | Steinbach |
| 2012/0209197 | A1 | 8/2012 | Lanigan et al. |
| 2012/0211946 | A1 | 8/2012 | Halili et al. |
| 2012/0215183 | A1 | 8/2012 | Halili et al. |
| 2012/0220936 | A1 | 8/2012 | Miller et al. |
| 2012/0289900 | A1 | 11/2012 | Chong et al. |
| 2012/0296307 | A1* | 11/2012 | Holt .................... A61J 1/2096 |
| | | | 604/407 |
| 2013/0006191 | A1 | 1/2013 | Jugl et al. |
| 2013/0006213 | A1 | 1/2013 | Arnitz et al. |
| 2013/0060232 | A1 | 3/2013 | Adlon et al. |
| 2013/0174518 | A1 | 7/2013 | Tachikawa et al. |
| 2013/0218092 | A1 | 8/2013 | Davies et al. |
| 2013/0218093 | A1 | 8/2013 | Markussen et al. |
| 2013/0237916 | A1 | 9/2013 | Hanson et al. |
| 2013/0253472 | A1 | 9/2013 | Cabiri |
| 2013/0267896 | A1 | 10/2013 | Dogwiler et al. |
| 2013/0289518 | A1 | 10/2013 | Butler et al. |
| 2013/0296779 | A1 | 11/2013 | Kuehne et al. |
| 2013/0310800 | A1 | 11/2013 | Yodfat et al. |
| 2014/0025008 | A1 | 1/2014 | Sims |
| 2014/0074037 | A1 | 3/2014 | Bornhoft |
| 2014/0081239 | A1 | 3/2014 | Cronenberg |
| 2014/0110370 | A1 | 4/2014 | Holt et al. |
| 2014/0121598 | A1 | 5/2014 | Katase |
| 2014/0121600 | A1 | 5/2014 | McConnell et al. |
| 2014/0121633 | A1 | 5/2014 | Causey et al. |
| 2014/0135693 | A1 | 5/2014 | Chappel et al. |
| 2014/0135695 | A1 | 5/2014 | Grant et al. |
| 2014/0148784 | A1 | 5/2014 | Anderson et al. |
| 2014/0207104 | A1 | 7/2014 | Vouillamoz et al. |
| 2014/0213975 | A1 | 7/2014 | Clemente et al. |
| 2014/0213977 | A1 | 7/2014 | Miller et al. |
| 2014/0221930 | A1 | 8/2014 | Kuster et al. |
| 2014/0243786 | A1 | 8/2014 | Gilbert et al. |

(56) References Cited

U.S. PATENT DOCUMENTS

| | | |
|---|---|---|
| 2014/0276431 A1 | 9/2014 | Estes et al. |
| 2014/0276563 A1 | 9/2014 | Cole et al. |
| 2014/0276576 A1 | 9/2014 | Cole et al. |
| 2014/0288511 A1 | 9/2014 | Tan-Malecki et al. |
| 2014/0323971 A1 | 10/2014 | Zhou |
| 2014/0323989 A1 | 10/2014 | Baker et al. |
| 2014/0358113 A1 | 12/2014 | Mernoe et al. |
| 2014/0358119 A1 | 12/2014 | Searle et al. |
| 2014/0364808 A1 | 12/2014 | Niklaus et al. |
| 2014/0378891 A1 | 12/2014 | Searle et al. |
| 2014/0378943 A1 | 12/2014 | Geipel |
| 2015/0011976 A1 | 1/2015 | Vouillamoz et al. |
| 2015/0038939 A1 | 2/2015 | Estes et al. |
| 2015/0057613 A1 | 2/2015 | Clemente et al. |
| 2015/0057615 A1 | 2/2015 | Mernoe, V et al. |
| 2015/0065959 A1 | 3/2015 | Carter et al. |
| 2015/0105720 A1 | 4/2015 | Montalvo et al. |
| 2015/0119797 A1 | 4/2015 | Cabiri |
| 2015/0119821 A1 | 4/2015 | Schmitz et al. |
| 2015/0157788 A1 | 6/2015 | Gescheit et al. |
| 2015/0190588 A1 | 7/2015 | Hanson et al. |
| 2015/0224253 A1 | 8/2015 | Cabiri |
| 2015/0246176 A1 | 9/2015 | Navarro et al. |
| 2015/0258273 A1 | 9/2015 | Payne et al. |
| 2015/0374919 A1 | 12/2015 | Gibson |
| 2016/0166765 A1 | 6/2016 | Tan-Malecki et al. |
| 2016/0199578 A1 | 7/2016 | Tan-Malecki et al. |
| 2016/0199582 A1 | 7/2016 | Tan-Malecki et al. |
| 2016/0199583 A1 | 7/2016 | Tan-Malecki et al. |
| 2016/0296704 A1 | 10/2016 | Gibson |
| 2018/0256821 A1 | 9/2018 | Tan-Malecki et al. |

FOREIGN PATENT DOCUMENTS

| | | | | |
|---|---|---|---|---|
| CN | 102149416 A | 8/2011 | | |
| CN | 102481230 A | 5/2012 | | |
| CN | 202723859 U | 2/2013 | | |
| EP | 0602883 A2 | 6/1994 | | |
| EP | 1927372 A1 | 6/2008 | | |
| EP | 2248832 A1 | 11/2010 | | |
| EP | 2468342 A1 * | 6/2012 | ............ | A61M 5/20 |
| EP | 2554207 A1 | 2/2013 | | |
| GB | 708707 A | 5/1954 | | |
| GB | 718837 A | 11/1954 | | |
| GB | 722166 A | 1/1955 | | |
| GB | 989185 A | 4/1965 | | |
| GB | 1159664 A | 7/1969 | | |
| JP | 126230 B | 5/1938 | | |
| JP | 39-009343 B | 6/1964 | | |
| JP | S39009343 B | 6/1964 | | |
| JP | S4020079 B | 7/1965 | | |
| JP | S508273 B1 | 4/1975 | | |
| JP | S51398 B1 | 1/1976 | | |
| JP | S645565 A | 1/1989 | | |
| JP | S6470070 A | 3/1989 | | |
| JP | H03168154 A | 7/1991 | | |
| JP | H06209996 A | 8/1994 | | |
| JP | H07124256 A | 5/1995 | | |
| JP | H07148258 A | 6/1995 | | |
| JP | 2001524362 A | 12/2001 | | |
| JP | 2002-505601 A | 2/2002 | | |
| JP | 2002507459 A | 3/2002 | | |
| JP | 2003527159 A | 9/2003 | | |
| JP | 2004305621 A | 11/2004 | | |
| JP | 2004-538043 A | 12/2004 | | |
| JP | 2007117379 A | 5/2007 | | |
| JP | 2007209675 A | 8/2007 | | |
| JP | 2009511192 A | 3/2009 | | |
| JP | 2009207619 A | 9/2009 | | |
| JP | 2012500679 A | 1/2012 | | |
| JP | 2012528636 A | 11/2012 | | |
| JP | 2012528639 A | 11/2012 | | |
| JP | 2013509925 A | 3/2013 | | |
| TW | M261223 U | 4/2005 | | |
| TW | 201100135 A | 1/2011 | | |
| WO | WO-88/02265 A1 | 4/1988 | | |
| WO | WO-95/12482 A1 | 5/1995 | | |
| WO | WO-98/57683 A1 | 12/1998 | | |
| WO | WO-99/48546 A1 | 9/1999 | | |
| WO | WO-0130424 A1 | 5/2001 | | |
| WO | WO-01/54755 A1 | 8/2001 | | |
| WO | WO-2004/096113 A2 | 11/2004 | | |
| WO | WO-2007047403 A1 | 4/2007 | | |
| WO | WO-2007/095297 A2 | 8/2007 | | |
| WO | WO-2008/083209 A2 | 7/2008 | | |
| WO | WO-2009/029010 A1 | 3/2009 | | |
| WO | WO-2010/022870 A1 | 3/2010 | | |
| WO | WO-2010/029054 A1 | 3/2010 | | |
| WO | WO-2010098323 A1 | 9/2010 | | |
| WO | WO-2010/139669 A1 | 12/2010 | | |
| WO | WO-2010/139672 A1 | 12/2010 | | |
| WO | WO-2010149975 A1 | 12/2010 | | |
| WO | WO-2011/054755 A1 | 5/2011 | | |
| WO | WO-2011058560 A1 * | 5/2011 | ............ | A61J 1/2096 |
| WO | WO-2011/117287 A1 | 9/2011 | | |
| WO | WO-2011/122395 A1 | 10/2011 | | |
| WO | WO-2013032779 A2 | 3/2013 | | |
| WO | WO-2013055873 A1 | 4/2013 | | |
| WO | WO-2013/089105 A1 | 6/2013 | | |
| WO | WO-2014/149357 A1 | 9/2014 | | |

OTHER PUBLICATIONS

Australian Patent Application No. 2012322796, Examination Report No. 2, issued Sep. 13, 2016.
Australian Patent Application No. 2014238267, Examination Report No. 2, dated Jun. 14, 2019.
Australian Patent Application No. 2014340171, Examination Report No. 1, issued Jun. 12, 2018.
Australian Patent Application No. 2017203992, Examination Report No. 1, issued Nov. 6, 2018.
Chinese Patent Application No. 201480017559.3, First Office Action (English translation), dated Oct. 12, 2018.
Chinese Patent Application No. 201480017559.3, Search Report, dated Sep. 27, 2018.
Chinese Patent Application No. 201480017559.3, Second Office Action, dated Jun. 5, 2019.
Chinese Patent Application No. 201480017559.3, Supplemental Search Report, dated May 28, 2019.
Chinese Patent Application No. 201480058204.9, First Office Action, dated Nov. 28, 2018.
Chinese Patent Application No. 201480058204.9, Search Report, dated May 28, 2019.
Chinese Patent Application No. 201480058204.9, Search Report, dated Nov. 19, 2018.
Chinese Patent Application No. 201480058204.9, Second Office Action, dated Jun. 4, 2019 . . . .
Communication pursuant to Article 94(3) EPC dated Mar. 6, 2018 and issued in European Patent Application No. 14792707.3.
Communication pursuant to Article 94(3) EPC issued in European Patent Application No. EP1615530.5, dated Aug. 14, 2017.
Communication pursuant to Article 94(3) EPC issued in European Patent Application No. EP16156583.3, dated Aug. 22, 2017.
Communication under Rule 71(3) EPC issued in EPO Patent Application No. 16155526.3, dated Nov. 5, 2018.
Eurasian patent application No. 201490755, Official Action (translation) (Jun. 27, 2017).
Eurasian patent application No. 201490755, Official Action (translation) (Oct. 31, 2016).
European Office Action for Application No. 12 784 119.5 dated Dec. 4, 2015.
European Patent Application No. 14708447.9, Communication pursuant to Article 94(3) EPC, dated Jan. 12, 2018.
European Patent Application No. 16155526.3, Communication pursuant to Article 94(3) EPC, dated Jan. 26, 2018.
European Patent Application No. 16155530.5, Communication Pursuant to Article 94(3) EPC, dated Jul. 12, 2019.
European Patent Application No. 16155530.5, Communication pursuant to Article 94(3) EPC, dated Sep. 3, 2018.

(56) References Cited

OTHER PUBLICATIONS

European Patent Application No. 16156583.3, Communication Pursuant to Article 94(3) EPC, dated Jul. 6, 2020.
European Patent Application No. 16156583.3, Communication pursuant to Article 94(3) EPC, Sep. 3, 2018.
European Patent Application No. 16156583.3, Communication Pursuant to Article 94(3), dated Jul. 19, 2019.
European Patent Application No. 16156583.3, Result of Consultation, Jul. 10, 2019.
European Patent Application No. 17187106.4, Communication Pursuant to Article 94(3) EPC, dated Dec. 11, 2018.
European Patent Application No. 17187106.4, Extended European Search Report, dated Nov. 30, 2017.
European Patent Application No. 18155148.2, Communication Pursuant to Article 94(3) EPC, dated May 21, 2019.
European Patent Application No. 18186736.7, Communication Pursuant to Article 94(3) EPC, dated Sep. 9, 2019.
European Patent Application No. 18186736.7, Extended European Search Report, dated Nov. 20, 2018.
European Search Report issued in European Patent Application No. 18155148.2, dated May 4, 2018.
Examiner's Decision of Rejection issued in Japanese Patent Application No. 2016-504292, dated May 8, 2018.
Extended European Search Report, European patent application No. 16155526.3, dated Jun. 20, 2016.
Extended European Search Report, European patent application No. EP1615530, dated Jun. 20, 2016.
Extended European Search Report, European patent application No. EP16156580.9, dated Jun. 20, 2016.
Extended European Search Report, European patent application No. EP16156583.3, dated Jun. 20, 2016.
International Preliminary Report on Patentability, corresponding international application No. PCT/US2012/059680, Apr. 15, 2014.
International Preliminary Report on Patentability, International Application No. PCT/US2014/017641, dated Sep. 22, 2015.
International Preliminary Report on Patentability, International Application No. PCT/US2014/061675, dated Apr. 26, 2016.
International Search Report and Written Opinion, corresponding international application No. PCT/US2012/059680, mailing date Jan. 30, 2013.
International Search Report and Written Opinion, International Application No. PCT/US2014/061675, mailed Jan. 19, 2015.
International Search Report for Application No. PCT/US2014/017641, dated Jul. 21, 2014.
Israel Patent Application No. 231679, Office Action, dated Apr. 20, 2017.
Israel Patent Application No. 260100, Office Action, dated Oct. 18, 2018.
Israeli Patent Application No. 243979, Office Action, dated Jun. 23, 2019.
Japanese Patent Application No. 2016-504292, Appeal No. 2018-11867 (against the Examiner's Decision of Rejection), mailed Sep. 10, 2019.
Japanese Patent Application No. 2016-504292, Re-examination Report, dated Nov. 20, 2018.
Japanese Patent Application No. 2016-550467, Notice of Rejection, dated Apr. 16, 2019.
Japanese Patent Application No. 2018-165651, Notice of Rejection, mailed Jul. 23, 2019.
Japanese Patent Application No. 2018-178432, Notice of Rejection, mailed Sep. 10, 2019.
Korean Patent Application No. 10-2014-7012457, Notice of Preliminary Rejection, dated Apr. 17, 2019.
Korean Patent Application No. 10-2015-7030084, Notice of Preliminary Rejection, dated Nov. 18, 2020.
Mexican Application No. Application No. MX/a/2016/005312, Office Action, issued Aug. 20, 2019.
Mexican Patent Application No. MX/a/2014/004505, Official Action, dated Mar. 28, 2017.
Mexican Patent Application No. MX/a/2014/004505, Official Action, dated Oct. 4, 2017.
Mexican Patent Application No. MX/a/2015/013533, Office Action, dated Jul. 1, 2019.
Mexican Patent Application No. MX/a/2015/013533, Office Action, dated Nov. 27, 2018.
Notice of Rejection (translation), Japanese patent application No. 2014-535858, mailed Aug. 2, 2016.
Notice of Rejection mailed on Jan. 23, 2018 in counterpart Japanese Patent Application No. 2014-535858, and translation thereof.
Notice of Rejection mailed on Jun. 20, 2017 in Japanese Application No. 2014-535858 and translation thereof.
Notice of Rejection mailed on Oct. 17, 2017 in Japanese Patent Application No. 2016-504292 and translation thereof.
Office Action issued in Australia Patent Application No. 2014238267, dated Aug. 9, 2018.
Office Action issued in Canada Patent Application No. 2,851,521, dated Aug. 24, 2018.
Office Action issued in Israel Patent Application No. 239799, dated Oct. 7, 2018.
Office Action issued in Japan Patent Application No. 2016-550467, dated Aug. 14, 2018.
Office Action issued in Mexican Patent Application No. MX/a/2015/013533, dated Aug. 22, 2018.
Office Action issued in U.S. Appl. No. 14/763,429, dated Aug. 16, 2018.
Office Action issued in U.S. Appl. No. 14/763,429, dated Feb. 13, 2018.
Office Action issued in U.S. Appl. No. 14/916,208, dated Aug. 11, 2018.
Office Action issued in U.S. Appl. No. 14/916,208, dated Jun. 7, 2018.
Office Action issued in U.S. Appl. No. 15/040,308, dated Apr. 2, 2018.
Office action issued in U.S. Appl. No. 15/040,308, dated Aug. 6, 2018.
Office Action issued in U.S. Appl. No. 15/040,335, dated Jun. 21, 2018.
Office Action issued in U.S. Appl. No. 15/040,335, dated Oct. 24, 2018.
Office Action issued in U.S. Appl. No. 15/047,792, dated Apr. 2, 2018.
Office Action issued in U.S. Appl. No. 15/047,792, dated Aug. 2, 2018.
Office Action issued in U.S. Appl. No. 15/047,815, dated May 24, 2018.
Office Action issued on Mar. 15, 2017 in Taiwanese Application No. 103108887 and translation thereof.
Official Action (translation), Eurasian patent application No. 201490755 (Feb. 29, 2016).
Patent Examination Report No. 1, Australian Patent Application No. 2012322796, issued May 31, 2016.
Search Report and Written Opinion for Singapore Patent Application No. 11201507878S dated Nov. 28, 2016.
Search Report issued in counterpart Taiwanese Patent Application No. 106134719 on Jul. 4, 2018.
Singapore Patent Application No. 11201507878S, Written Opinion, dated Feb. 4, 2019.
Singapore Patent Application No. 11201602876W, Written Opinion, dated Jul. 11, 2017.
Text of First Office Action (translation), Chinese patent application No. 201280050454.9, dated Jul. 15, 2015).
Text of Second Office Action (translation), Chinese patent application No. 201280050454.9, dated Mar. 18, 2016.
U.S. Appl. No. 14/763,429, Final Office Action, dated May 4, 2020.
U.S. Appl. No. 14/916,208, Final Office Action, Jan. 28, 2021.
U.S. Appl. No. 14/916,208, Nonfinal Office Action, dated Jan. 13, 2020.
U.S. Appl. No. 14/916,208, Nonfinal Office Action, dated Sep. 22, 2020.
U.S. Appl. No. 14/916,208, Notice of Allowance, dated Apr. 28, 2021.

(56) References Cited

OTHER PUBLICATIONS

U.S. Appl. No. 15/040,308, Nonfinal Office Action, dated Feb. 26, 2019.
U.S. Appl. No. 15/047,792, Nonfinal Office Action, dated Feb. 15, 2019.
U.S. Appl. No. 15/047,815, Decision on Appeal, dated Nov. 27, 2020.
U.S. Appl. No. 15/047,815, Decision on Request for Rehearing, dated Mar. 19, 2021.
U.S. Appl. No. 16/401,471, Nonfinal Office Action, dated Dec. 16, 2020.
U.S. Appl. No. 16/687,254, Final Office Action, dated Dec. 22, 2020.
U.S. Appl. No. 16/687,254, Nonfinal Office Action, dated Jul. 27, 2020.
U.S. Appl. No. 16/687,254, Notice of Allowance dated Mar. 10, 2021.
U.S. Appl. No. 16/839,267, Final Office Action, dated Mar. 23, 2021.
U.S. Appl. No. 16/839,267, Nonfinal Office Action, dated Dec. 15, 2020.
U.S. Appl. No. 16/839,267, Nonfinal Office Action, dated Jun. 24, 2021.
U.S. Appl. No. 14/350,687, Office Action, dated Aug. 3, 2016.
U.S. Appl. No. 14/350,687, Office Action, dated Feb. 19, 2016.
U.S. Appl. No. 14/350,687, Office Action, dated Mar. 31, 2017.
U.S. Appl. No. 14/763,429, Final Office Action, dated Aug. 6, 2019.
U.S. Appl. No. 14/763,429, Nonfinal Office Action, dated Jan. 25, 2019.
U.S. Appl. No. 14/916,208, Final Office Action, dated Nov. 8, 2018.
U.S. Appl. No. 15/047,815, Final Office Action, dated Nov. 16, 2018.
U.S. Appl. No. 15/047,815, Final Office Action, dated Oct. 4, 2019.
U.S. Appl. No. 15/047,815, Nonfinal Office Action, dated May 2, 2019.
U.S. Appl. No. 15/974,354, Nonfinal Office Action, dated Oct. 24, 2019.
Written Opinion dated Jan. 18, 2018 and issued in counterpart Singaporean Patent Application No. 11201507878S.
Written Opinion for Application No. PCT/US2014/017641, dated Sep. 22, 2015.
Written Opinion for Singapore Application No. 11201602876W, dated Jan. 3, 2017.
Japanese Patent Application No. 2020-190671, Office Action, mailed Oct. 5, 2021.
Brazilian Patent Application No. BR112016008946-4, Office Action, dated Jun. 28, 2022.

* cited by examiner

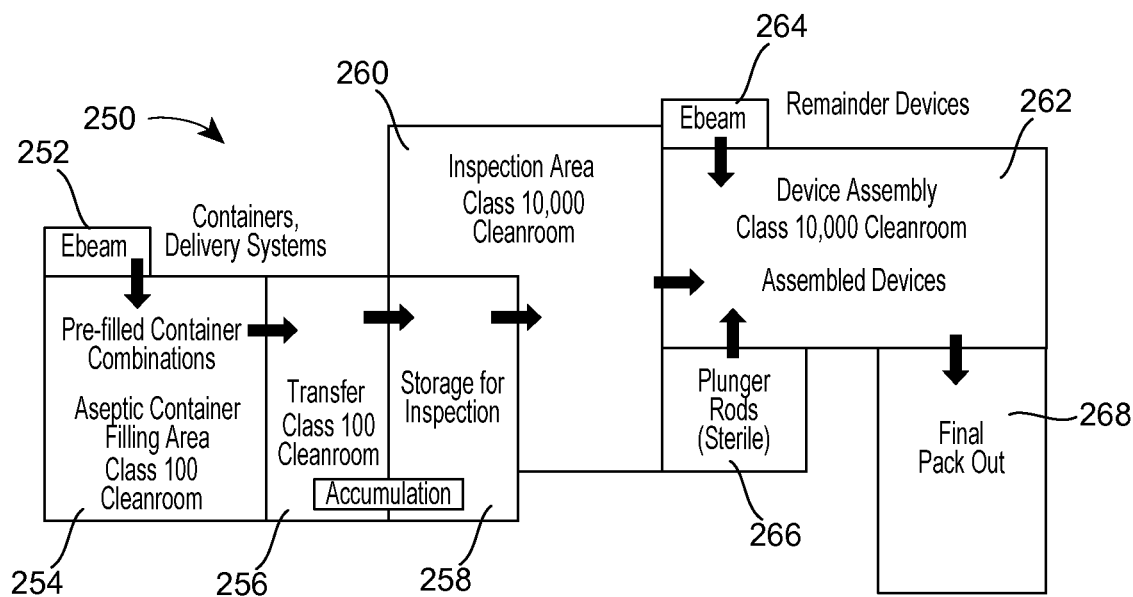
*FIG. 4*
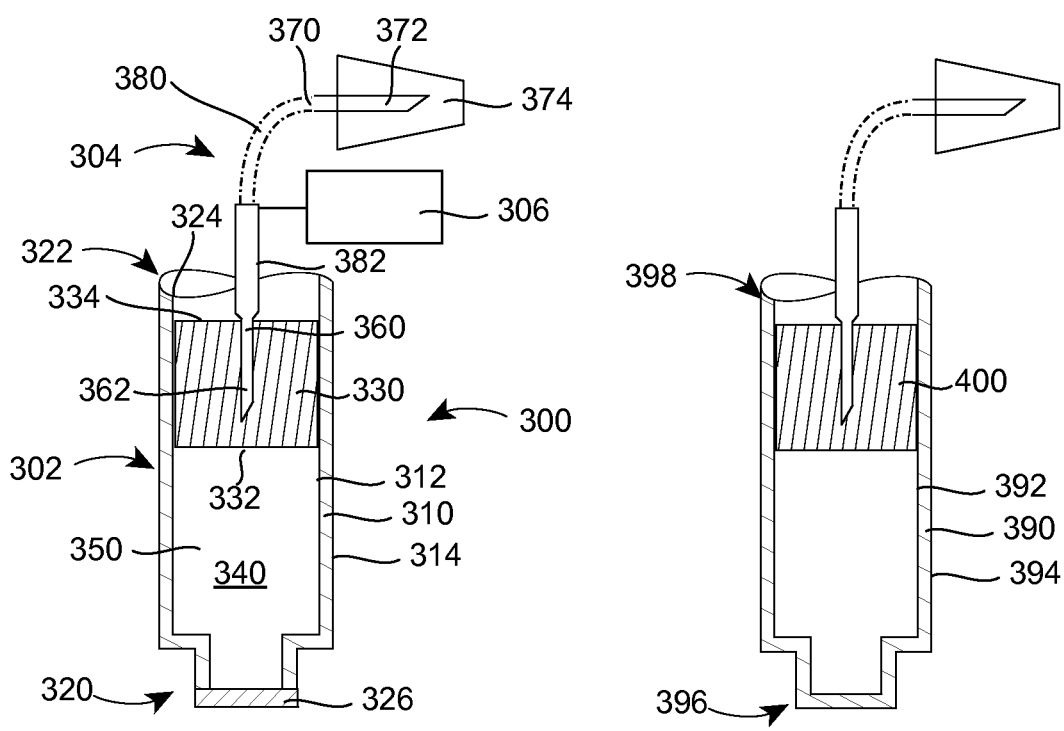
*FIG. 5*   *FIG. 6*

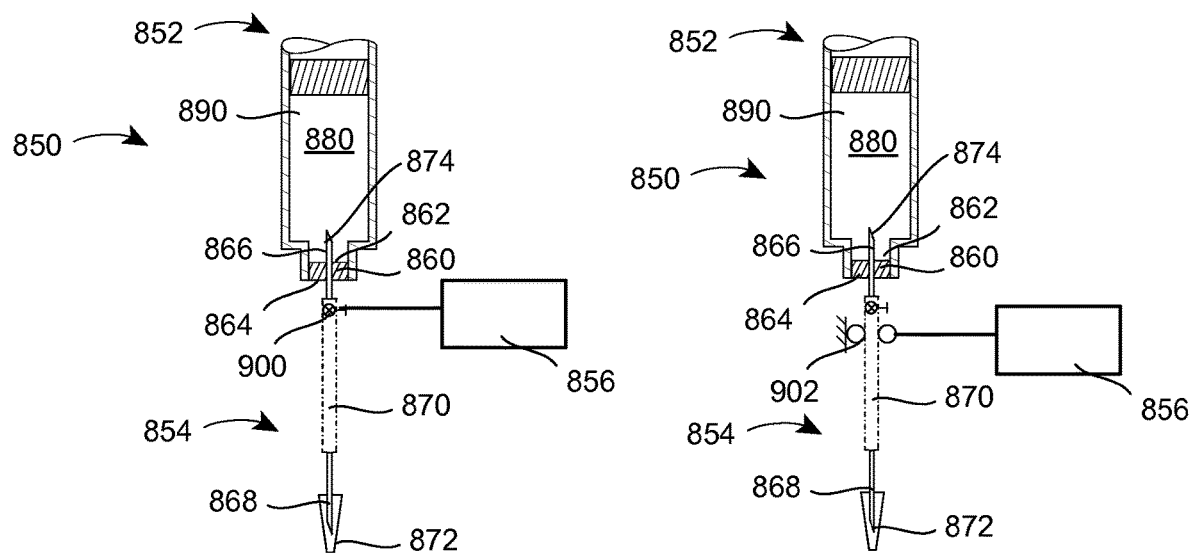
*FIG. 12*     *FIG. 13*
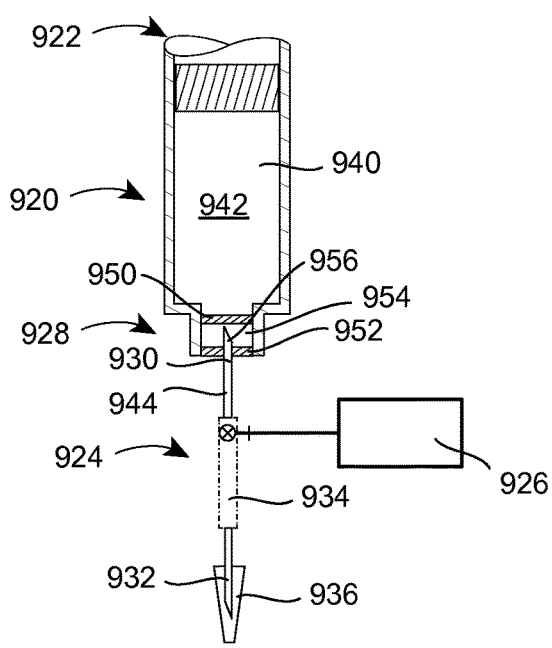
*FIG. 14*

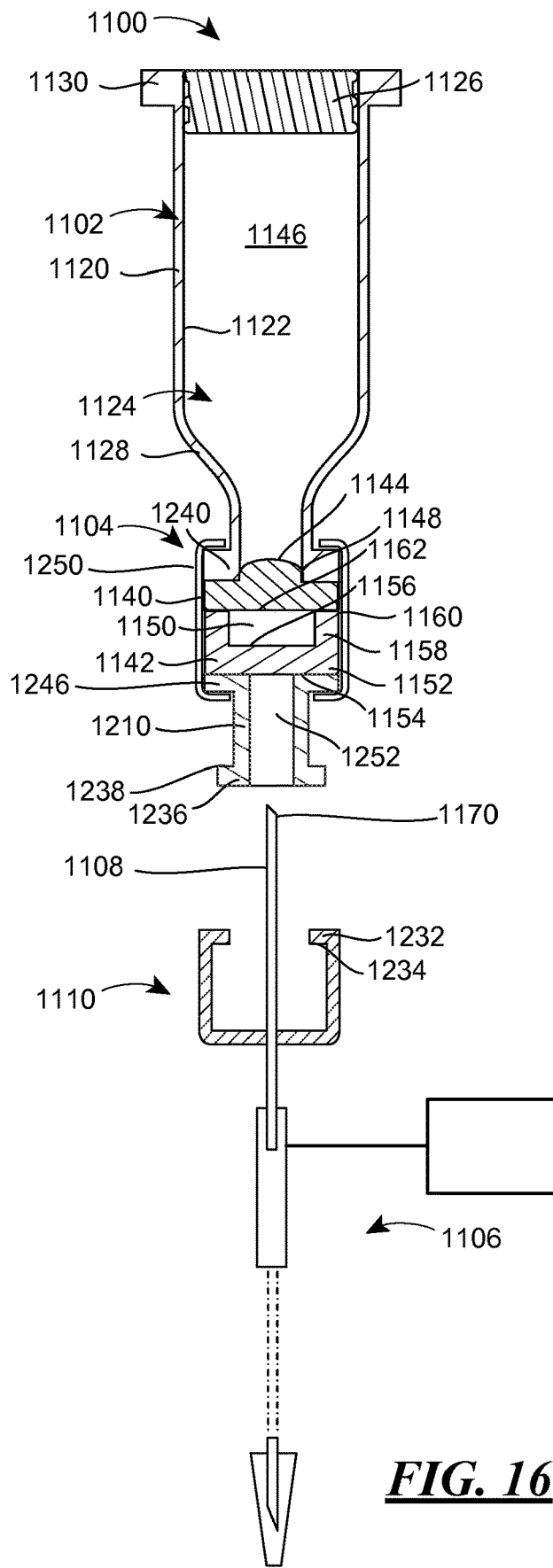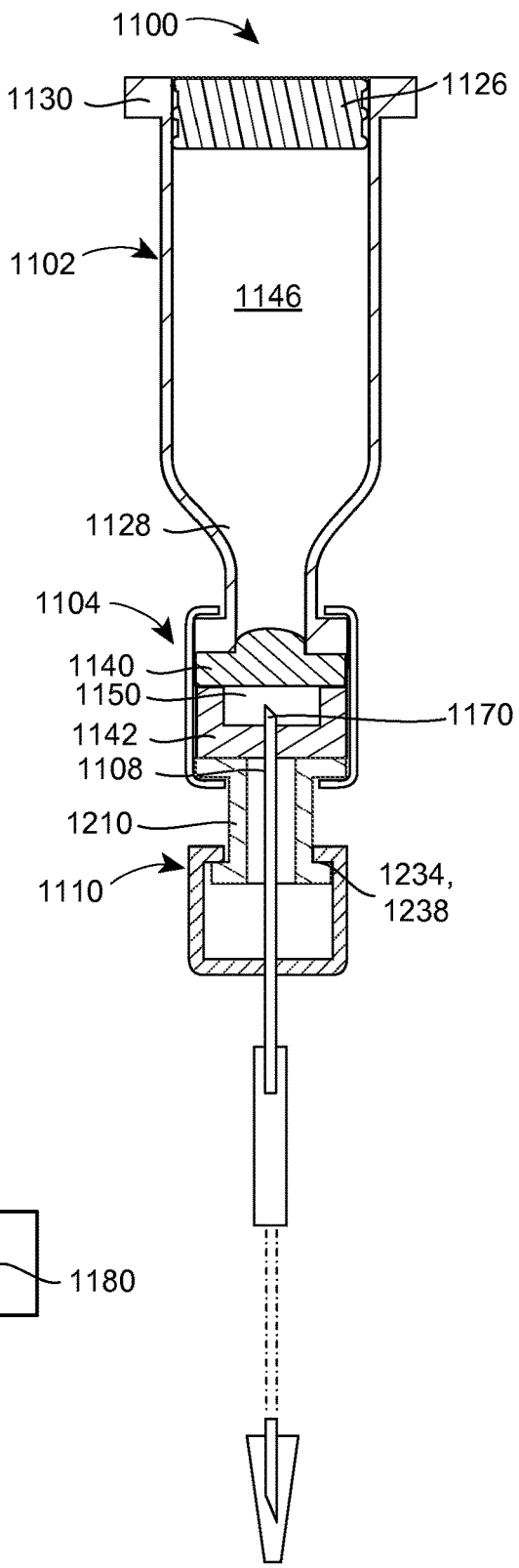
*FIG. 16*  *FIG. 17*

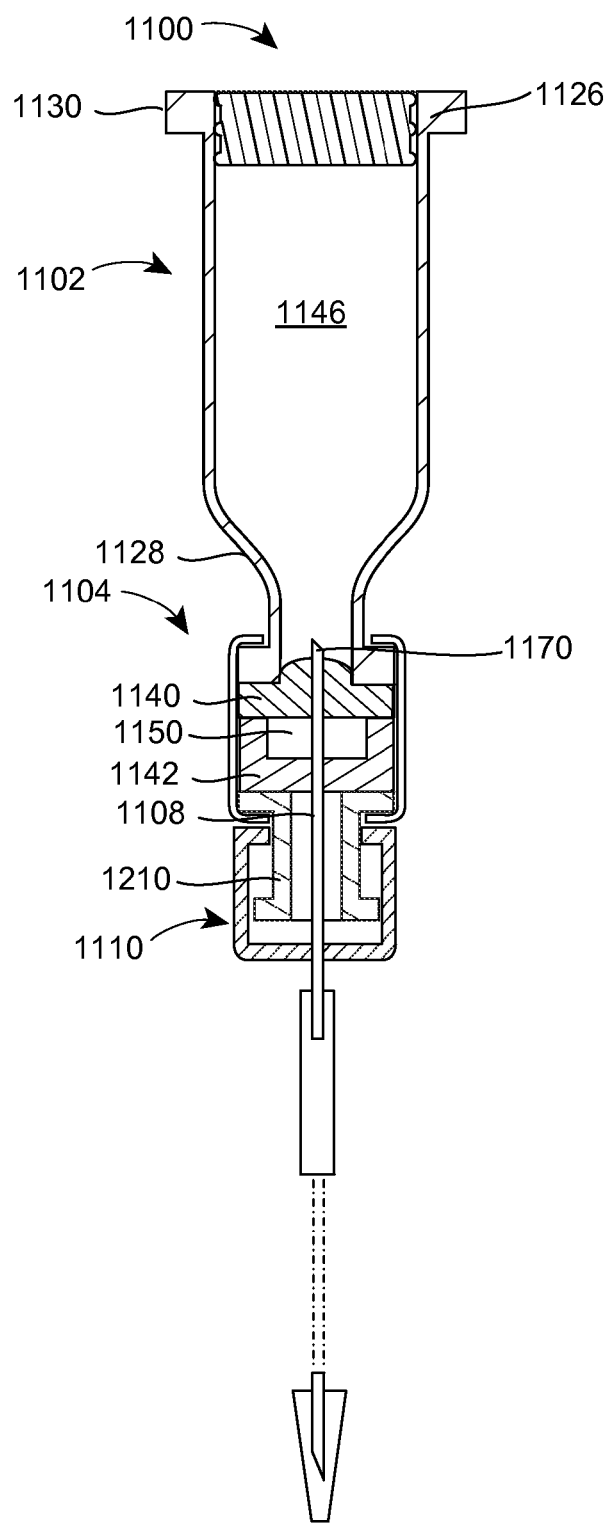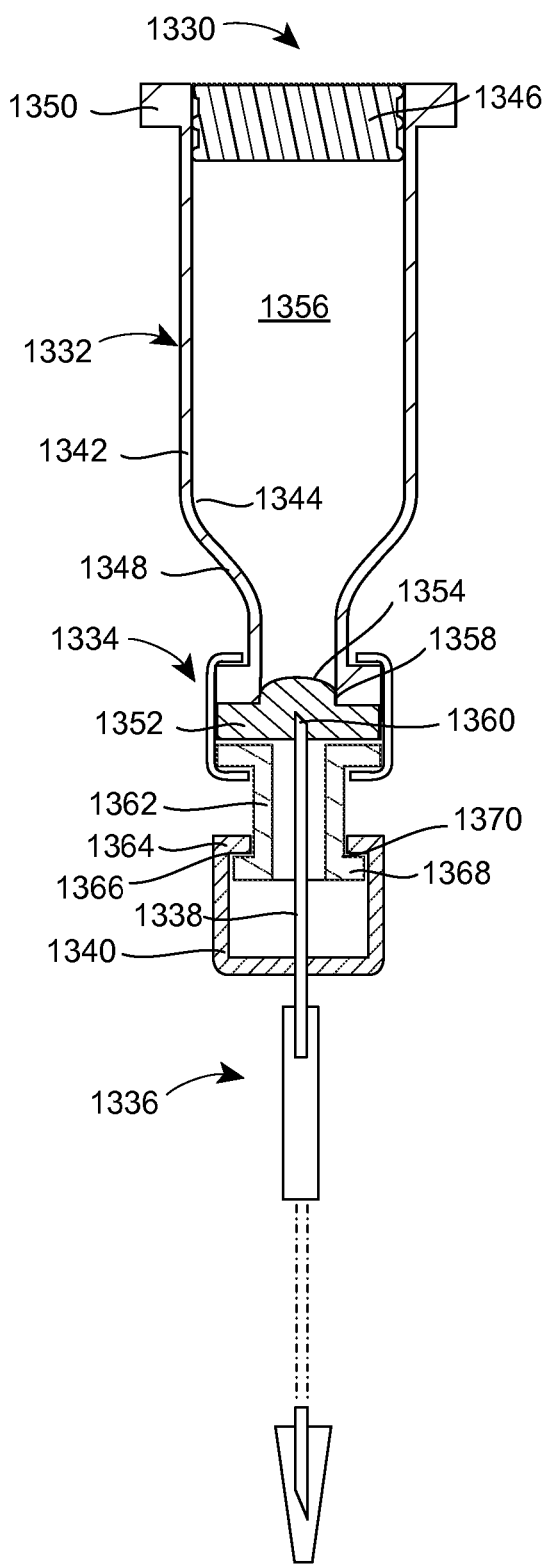
*FIG. 18*  *FIG. 24*

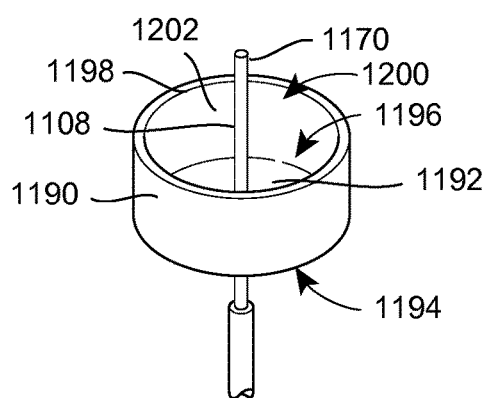
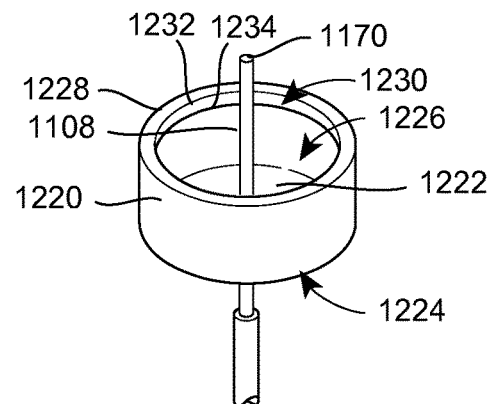
*FIG. 19*                *FIG. 20*
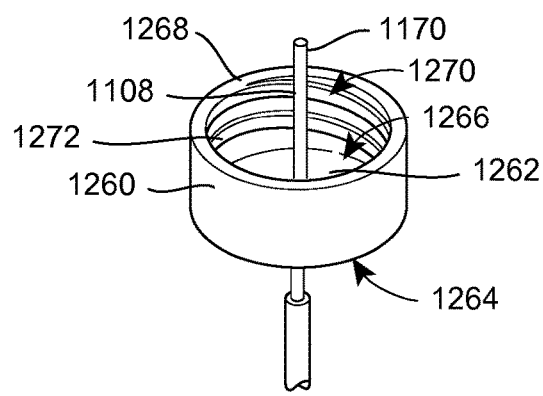
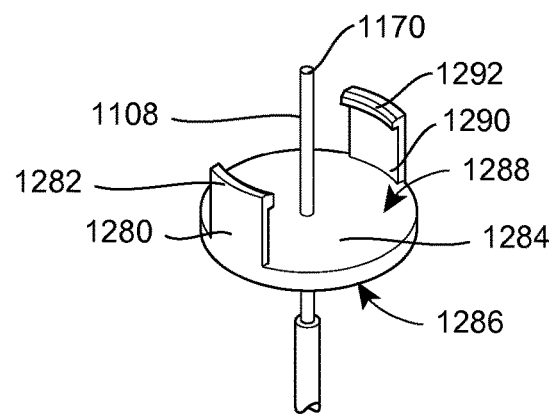
*FIG. 21*                *FIG. 22*

INJECTOR AND METHOD OF ASSEMBLY

CROSS-REFERENCE TO RELATED APPLICATIONS

This is a continuation of U.S. application Ser. No. 14/916,208, filed Mar. 3, 2016, which is the US National Phase of International Patent Application No. PCT/US2014/061675, having an international filing date of Oct. 22, 2014, and which claims the priority benefit of U.S. Provisional Application No. 61/895,390, filed Oct. 24, 2013. The entire contents of each of the foregoing is expressly incorporated herein by reference.

FIELD OF THE DISCLOSURE

This patent is directed to an injector and a method of assembling the injector and, in particular, to a prefilled injector and a method of assembling the prefilled injector.

BACKGROUND

Injectors are used to deliver medical fluids or drug products, such as liquid drugs, to a patient. In particular, the injector will provide the fluid to the patient through a needle, cannula or catheter that defines a flow path into the patient. Certain injectors have a reservoir that is assembled by the manufacturer already connected to the flow path. These reservoirs are typically provided empty by the manufacturer to the patient or healthcare provider (e.g., doctor, nurse, healthcare assistant, etc.), and then the reservoir is filled at the time of use. Alternatively, the injector may be used in combination with a reservoir that is provided to the patient or healthcare provider prefilled.

In either case, the injector must be prepared prior to use. For example, if the reservoir is provided empty, then the reservoir must be filled. To do this, a syringe is filled with the medical fluid or drug product to be delivered, and then the medical fluid or drug product is injected into the reservoir through an inlet port. Prior to the injection, the inlet port must be sterilized by swabbing the outer surface with an alcohol wipe, for example. Similarly, before the prefilled reservoir is connected to the flow path in the alternative injector, the mating connectors must be sterilized, by swabbing the surface with an alcohol wipe.

In either event, the use of the injector requires additional material and time.

As set forth in more detail below, the present disclosure provides an improved injector embodying advantageous alternatives to the conventional devices and methods discussed above.

SUMMARY

According to an aspect of the present disclosure, an injector includes a container, a seal assembly, a fluid delivery system, and an actuator. The seal assembly includes a flexible seal assembly wall with an interior surface, the interior surfaces of a container wall and the seal assembly wall defining a closed sterile reservoir filled with a medical fluid or drug product, and a barrier disposed exterior of the seal assembly wall to define an enclosed space between the flexible wall and the barrier. The fluid delivery system includes a sterile container needle having a point disposed only through the barrier in a storage state, and disposed through the flexible wall into the sterile reservoir in a delivery state. The sterile container needle is attached to a connector, the connector mechanically coupled to the container to secure the sterile container needle to the container with the needle in the storage state. The actuator is adapted to move the container needle from the storage state to the delivery state.

According to another aspect of the present disclosure, a method of assembling an injector includes filling a sterile reservoir of a container with a medical fluid or drug product under sterile conditions, the reservoir defined by an interior surface of a wall of the container, mechanically coupling a sterile fluid delivery system to the container under sterile conditions, the fluid delivery system not in fluid communication with the reservoir in a storage state and in fluid communication with the reservoir in a delivery state, and assembling the remainder of the injector under clean room conditions.

BRIEF DESCRIPTION OF THE DRAWINGS

The disclosure will be more fully understood from the following description taken in conjunction with the accompanying drawings. Some of the figures may have been simplified by the omission of selected elements for the purpose of more clearly showing other elements. Such omissions of elements in some figures are not necessarily indicative of the presence or absence of particular elements in any of the exemplary embodiments, except as may be explicitly delineated in the corresponding written description. None of the drawings are necessarily to scale.

FIG. 4 is a schematic of a manufacturing facility wherein injectors according to the present disclosure may be filled and assembled;

FIG. 5 is a cross-sectional view of an embodiment of an injector according to the present disclosure, with a container needle in a storage state wherein the needle partially penetrates a unitary wall of the container;

FIG. 6 is a cross-sectional view of an embodiment of an injector according to the present disclosure, with a container needle in a storage state wherein the needle partially penetrates a unitary wall of the container;

FIG. 12 is a cross-sectional view of an injector according to an embodiment of the present disclosure where a sterile condition is maintained in a reservoir until actuation of the fluid delivery system;

FIG. 13 is a cross-sectional view of an injector according to an embodiment of the present disclosure where a sterile condition is maintained in a reservoir until actuation of the fluid delivery system;

FIG. 14 is a cross-sectional view of an injector according to an embodiment of the present disclosure where a sterile condition is maintained in a reservoir until actuation of the fluid delivery system;

FIG. 16 is a cross-sectional view of an embodiment of an injector according to the present disclosure prior to assembly;

FIG. 17 is a cross-sectional view of an embodiment of the injector of FIG. 16, with a container needle in a storage state wherein the needle partially penetrates a barrier, but not a flexible wall, of a seal assembly;

FIG. 18 is a cross-sectional view of an embodiment of the injector of FIG. 16, with a container needle in a delivery state wherein the needle penetrates the barrier and the flexible wall of the seal assembly;

FIG. 19 is an embodiment of a connector for use with a container needle and a container similar to that illustrated in FIGS. 16-18;

FIG. 20 is an embodiment of a connector for use with a container needle and the container illustrated in FIGS. 16-18;

FIG. 21 is an embodiment of a connector for use with a container needle and a container similar to that illustrated in FIGS. 16-18;

FIG. 22 is an embodiment of a connector for use with a container needle and a container similar to that illustrated in FIGS. 16-18;

FIG. 24 is a cross-sectional view of an embodiment of the injector of FIG. 16, with a container needle in a storage state wherein the needle partially penetrates a flexible wall of a seal assembly.

DETAILED DESCRIPTION OF VARIOUS EMBODIMENTS

Figure 1:
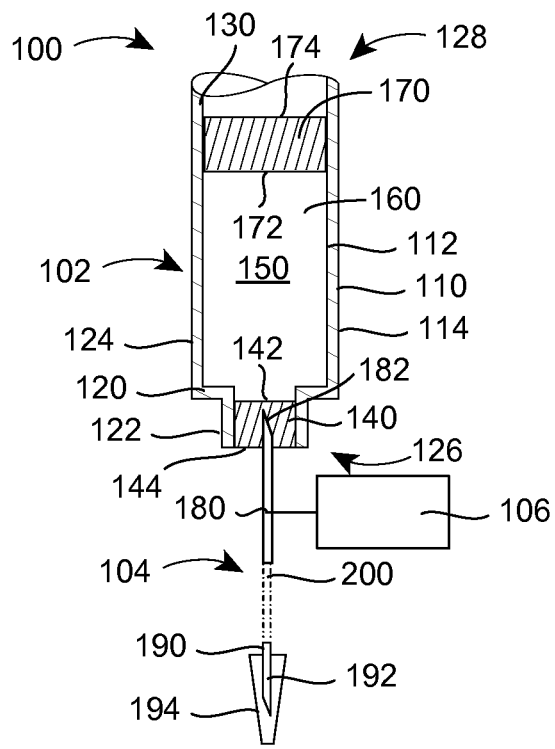
FIG. 1 is a cross-sectional view of an embodiment of an injector according to the present disclosure, with a container needle in a storage state wherein the needle partially penetrates a unitary wall of the container.

Although the following text sets forth a detailed description of different embodiments of the invention, it should be understood that the legal scope of the invention is defined by the words of the claims set forth at the end of this patent. It should also be understood that, unless a term is expressly defined in this patent using the sentence "As used herein, the term '_____' is hereby defined to mean . . . " or a similar sentence, there is no intent to limit the meaning of that term, either expressly or by implication, beyond its plain or ordinary meaning, and such term should not be interpreted to be limited in scope based on any statement made in any section of this patent (other than the language of the claims). To the extent that any term recited in the claims at the end of this patent is referred to in this patent in a manner consistent with a single meaning, that is done for sake of clarity only so as to not confuse the reader, and it is not intended that such claim term be limited, by implication or otherwise, to that single meaning. In addition, unless a claim element is defined by reciting the word "means" and a function without the recital of any structure, it is not intended that the scope of any claim element be interpreted based on the application of 35 U.S.C. § 112, sixth paragraph.

The detailed description is to be construed as exemplary only and does not describe every possible embodiment of the invention. Numerous alternative embodiments could be implemented, using either current technology or technology developed after the filing date of this patent, which would still fall within the scope of the claims defining the invention.

In general terms, an injector according to the present disclosure includes a container, a fluid delivery system and an actuator. While reference is made to an injector, which in some instances may refer to a delivery device that ensures that a set volume of medical fluid or drug product is delivered, it will be understood that this disclosure also encompasses infusion devices, which in some instances may refer to a delivery device that ensures that a particular rate of delivery is achieved. As used herein, the terms medical fluid and drug product may have the same or different meanings. The term medical fluids may encompass drug products, as well as other patient deliverable substances. It should also be understood that the terms injector and infuser may be used interchangeably when referring to embodiments in the specification. Furthermore, the subassembly of the container and the fluid delivery system may be addressed separately from the remainder of the injector, whether such subassembly is filled or unfilled with a medical fluid or drug product; for example, such subassembly may be transported as a unit during the assembly process in manufacturing the injector.

As illustrated in FIGS. 1-3 and 5-11, the container may include a wall with an interior surface and a seal assembly with an interior surface, the interior surfaces of the wall and the seal assembly defining a closed sterile reservoir filled with a medical fluid or drug product. Moreover, the fluid delivery system illustrated in these embodiments may include a sterile container needle, which may also be unsheathed, having a point disposed only partially through the seal assembly in a storage state, and disposed through the interior surface of the seal assembly into the sterile reservoir in a delivery state. As such, the needle is in fluid communication with the container in the delivery state, but not the storage state. According to these embodiments, the injector may include an actuator that is adapted to move the container needle from the storage state to the delivery state, which may involve movement of the needle relative to the container or the container relative to the needle.

As illustrated in FIGS. 1, 3, and 4-6, the seal assembly may be a flexible unitary wall having an interior surface that defines the interior surface of the seal assembly, and the point of the container needle may be disposed partially into the unitary wall. Alternatively, as illustrated in FIGS. 7-11, the seal assembly may include a flexible wall with an interior surface that defines the interior surface of the seal assembly, and a barrier disposed exterior of the flexible wall to define an enclosed space between the flexible wall and the barrier.

According to such embodiments, the point of the container needle is disposed through the barrier into the space in the storage state.

An embodiment of an injector 100 according to the present disclosure is illustrated in FIG. 1. The injector 100 includes a container 102, a fluid delivery system 104, and an actuator 106.

The container 102 (which also may be referred to as a cartridge) includes a wall 110 with an interior surface 112 and an exterior surface 114. While a unitary (i.e., one-piece) wall 110 that defines both the interior and exterior surfaces 112, 114 is shown in FIG. 1, in other embodiments, the wall 110 may include a plurality of layers with different layers defining the interior and exterior surfaces 112, 114.

According to certain embodiments of the present disclosure, the wall 110 is rigid. In other embodiments, the wall 110 is flexible, because of the material that defines the wall or the structure of wall (e.g., a bellows construction). The wall 110 may be made of glass, metal or polymer, for example. In particular, polymer versions may be made of polycarbonate, polypropylene, polyethylene (such as high density polyethylene), polytetrafluoroethylene, cyclic olefin polymer, cyclic olefin copolymer, Crystal Zenith® olefinic polymer (available from Daikyo Seiko, Ltd., Japan), nylon or engineering resins, for example. As to flexible versions of the wall 110, butyl rubber, silicon-based rubber, latex-based rubber, coated rubber, as well as multi-layer polymer films, such as may include polyethylene (such as low density polyethylene) and polypropylene, may be used.

The wall 110 may have a generally cylindrical shape, with a shoulder 120 separating a first cylindrical section 122 having a first cross-sectional diameter from a second cylindrical section 124 having a second cross-sectional diameter, the first cross-sectional diameter being smaller than the second cross-sectional diameter. The wall 110 may also define two opposed, open ends 126, 128. The wall 110, or more particularly the interior surface 112 of the wall 110, may also define a bore 130.

In some embodiments, the container 102 may include a flexible unitary wall 140 (which may also be referred to as a seal or septum) having an interior surface 142 and an exterior surface 144. The wall 140 may be disposed in the first open end 126 defined by the wall 110 and fixedly attached to the wall 110 of the container 102 such that there is limited relative movement between the wall 140 and the wall 110, for example at the points of attachment of the wall 140 to the wall 110 across the open end or opening 126. The interior surfaces 112, 142 of the wall 110 and the flexible wall 140 may define, at least in part, a closed sterile reservoir 150 that is filled with a medical fluid or drug product 160, described in greater detail below. The wall 140 may be made of bromobutyl, chlorobutyl or chlorobromobutyl rubber, fluoropolymer rubber, natural rubber, silicon-based rubber, silicon or santoprene, for example.

The container 102 may also include a stopper or piston 170 with interior and exterior surfaces 172, 174. The piston 170 may be received within the end 128 defined by the wall 110, and may be moveable along the bore 130 between the ends 126, 128 of the container 102. According to such an embodiment, the reservoir 150 within which the medical fluid or drug product 160 is disposed may be defined by the interior surfaces 112, 142, 172 of the walls 110, 140 and piston 170.

The container 102 may be used in conjunction with the fluid delivery system 104, the relevant portions of which are illustrated in FIG. 1. In particular, the fluid delivery system 104 may include a container needle 180 having a point 182.

Figure 2:
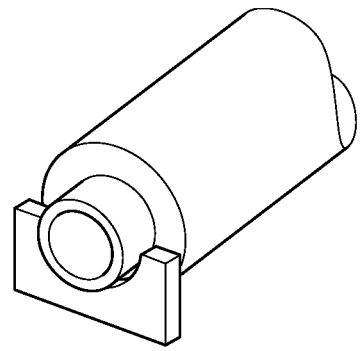
FIG. 2 is a perspective view of a jig used with the container of the injector of FIG. 1 to control the penetration of the flexible unitary wall of the container by the container needle.

As illustrated, the point 182 is disposed only partially into the flexible wall 140 in a storage state. The penetration of the point 182 of the needle 180 into the wall 140 may be controlled through a number of methods and/or mechanisms. For example, FIG. 2 illustrates a jig that may be used in combination with the container 102 to control the depth at which the point 182 penetrates the wall 140.

The fluid delivery system 104 may also include an injection needle 190 with a point 192. The point 192 of the injection needle 190 may be covered with a needle shield 194 to prevent contact with and contamination of the point 192. The container needle 180 and the injection needle 190 may be connected by a cannula or tube 200, which may be a flexible cannula according to certain embodiments of the present disclosure. The needle 190, similarly to the needle 180, may be made of stainless steel, for example. In some embodiments, the container needle 180 and the injection needle 190 may be formed integrally (i.e., as one piece).

Fluid delivery system 104 may be used in conjunction with the actuator 106, illustrated in FIG. 1. The actuator 106 may be adapted to move the container needle 180 between the storage state illustrated in FIG. 1 and a delivery state illustrated in FIG. 3, and thus move the fluid delivery system 104 between the storage and delivery states. In the delivery state, the container needle 180 is disposed through the interior surface 142 of the flexible wall 140 into the sterile reservoir 150 and is in fluid communication with the reservoir 150.

The movement of the needle 180 between the states may occur in a variety of ways. For example, the needle 180 may be held fixed relative to the housing of the injector 100, and the container 102 may move relative to the needle 180 and the housing. Alternatively, the container 102 may be held fixed relative to the housing, and the needle 180 may be moved relative to the container 102 and the housing. In other embodiments, both the container 102 and the needle 180 move relative to the housing of the injector 100. It will be understood that all of these actions are embraced within the statement that the actuator 106 is adapted to move the container needle 180 between the storage and delivery states.

The actuator 106 may be mechanical, electro-mechanical or electrical. For example, the actuator 106 may include a solenoid, motor-driven lever, motor with associated gearing, etc. In some embodiments, a tab or button attached to the container 102 or the needle 180 permits the user to achieve the relative motion between the container 102 and the needle 180 manually. The container 102 may be received within a tab or button that is depressed into the housing when the injector 100 is activated to move the container 102 relative to the (fixed) needle 180.

The actuator 106 may move the container needle 180 between storage and delivery states by moving the needle 180 from the storage state to the delivery state, or by moving the needle 180 from the delivery state to the storage state. In some embodiments, the actuator may move the container needle 180 between the storage and delivery states repeatedly (i.e., multiple times or repetitions). The actuator 106 may move the container needle 180 immediately upon receipt of an input or signal (e.g., as generated through the depression or manipulation of a button, switch or other input device, which may be mechanical, electro-mechanical or electrical in nature, coupled to the actuator 106), or may delay movement of the container needle 180 between storage and delivery states some period of time after an input is received. According to a particular embodiment, the actuator 106 may delay movement of the needle 180 from the storage state to the delivery state until after such a time delay.

According to embodiments of the present disclosure, both the reservoir 150 and the container needle 180 (and any attached tubing 200 and injection needle 190) are described as sterile, while the remainder of the delivery device/injector 100 (e.g., actuator 106) is described as clean. These terms describe the condition of the reservoir 150, the needle 180 or remainder of the delivery device as a consequence of their assembly under conditions that will ensure a specified level of freedom from contamination, wherein a sterile object or device is understood to have a relatively higher level of freedom from contamination than a clean object or device. By way of non-limiting example, the concepts of sterility and cleanliness may be discussed with reference to FIG. 4, which discussion applies to all of the embodiments described herein.

FIG. 4 illustrates a manufacturing facility 250, and may be used to discuss a manufacturing process that is conducted within the facility 250. It will be noted that the facility 250 is divided into a plurality of spaces 252, 254, 256, 258, 260, 262, 264, 266, 268, which divisions may be maintained through the use of permanent or semi-permanent walls or other barriers. As will be understood, certain spaces or regions may be divided without barriers or walls, but may simply be separated on an organizational level instead. Additionally, a greater or lesser number of spaces or an alternative arrangement of the spaces may be used, such differing numbers or arrangements of spaces being readily determinable by one of ordinary skill in the art.

In some embodiments, the components of the container 102 (walls 110, 140, and stopper/piston 170) and the fluid delivery system 104 enter the facility 250 through space 252, wherein the components are sterilized using e-beam technology, for example. Alternatively, while the container 102 and the fluid delivery system 104 are defined as separate structures with reference to the embodiments of FIGS. 1 and 3, it would be known to use the manufacturing process described herein with a product where the container 102 is attached to the fluid delivery system 104 prior to introduction into the space 254 (e.g., the container 102/fluid delivery system 104 is a syringe), and to sterilize the product. In some embodiments, the components may be sterilized through other currently-known (e.g., treatment with chlorine dioxide or vapor phase hydrogen peroxide) or later-developed sterilization procedures as the components enter the facility 250 at entry points 252, 264, 266. The container 102 and fluid delivery system 104 then pass into space 254 for filing with the medical fluid or drug product. The space 254 may be operated as an aseptic Class 100 clean room. A Class 100 clean room is one in which the number of particles of size 0.5 µm or larger permitted per cubic foot of air is less than 100. Once the fill has been performed and the stopper 170 has been disposed in the end 128 of the container 102, the container needle 180 is inserted partially into wall/septum 140. Because the container needle 180 does not penetrate through the wall 140, the reservoir 150 and the medical fluid or drug product 160 remains sterile (i.e., at the higher level of cleanliness). Moreover, because the fluid delivery system 104 is sterile and is assembled to the container 102 under sterile conditions, the fluid delivery system 104 is believed to remain sterile, in part because of the partial insertion of the container needle 180 and in part because of the shield 194.

The prefilled containers 102 in combination with the associated fluid delivery systems 104 (which combination may be referred to as a prefilled, sterile container combination, or in those embodiments wherein the fluid delivery system 104 and containers 102 are attached or formed integrally with each other (e.g., a syringe), the container 102 and the fluid delivery system 104 may also be referred to as prefilled sterile syringes) are moved through transfer space 256 (also operated as a Class 100 clean room, wherein certain embodiments are also aseptic) before being received within storage space 258. The prefilled, sterile container combinations are moved from the storage space 258 into inspection area 260 (aseptic in certain embodiments), wherein the prefilled, sterile container combinations are inspected prior to assembly with the actuator 106 and other elements of the injector 100. Because the medical fluid or drug product 160 is contained within the sealed container 102 and the sterility of the fluid delivery system 104 is preserved at this point (i.e., the container needle 180 is inserted into the wall 140 and the injector needle 190 is capped with the shield 194), the inspection area may be operated as a Class 10,000 clean room. Once inspected, the prefilled, sterile container combinations may be passed from inspection space 260 to assembly space 262.

Similar to the inspection space 260, the assembly space 262 may be operated as an aseptic Class 10,000 clean room, or in some embodiments a Class 100,000 clean room. Materials passed into the clean room from spaces 264, 266 may be in a sterile condition, or may be sterilized using e-beam technology, for example. Within the assembly space 262, the remainder of the injector 100 (e.g., the actuator 106) may be assembled (i.e., the container 102 and the fluid delivery system 104 may be disposed in the remainder of the injector 100) prior to the injector 100 passing into the packaging space 268.

Other processing, in addition to assembly, may occur at this point. According to certain embodiments, it may be desirable to arrange the fluid delivery system 104 in one configuration prior to assembly with the remainder of the injector 100, for ease of transport for example, but to have the fluid delivery system 104 assume a different arrangement once assembled in the injector 100. For example, it may be desirable for the fluid path between the container needle 180 and the injector needle 190 to have straight configuration prior to assembly with the remainder of the injector, but to assume a curved, bent (e.g., 60 degrees, 90 degrees, etc) or other non-straight configuration when assembled with the remainder of the injector 100. By maintaining the fluid delivery system 104 in a straight configuration, the spacing between the prefilled, sterile container combinations in a tray or other holder used to transport the prefilled, sterile container combinations may be maximized in that the additional room required to accommodate a curved, bent or other non-straight configuration may be avoided. This may also have an effect on the costs of filling the containers 102, in that each tray can accommodate a larger number of container 102/fluid delivery system 104 combinations, and thus the number of trays passing through the space 254 may be limited. The change in configuration may be performed in the assembly space 262, for example, so as to minimize the need to accommodate the curved, bent or otherwise non-straight fluid delivery systems 104 elsewhere in the facility 250.

Figure 3:
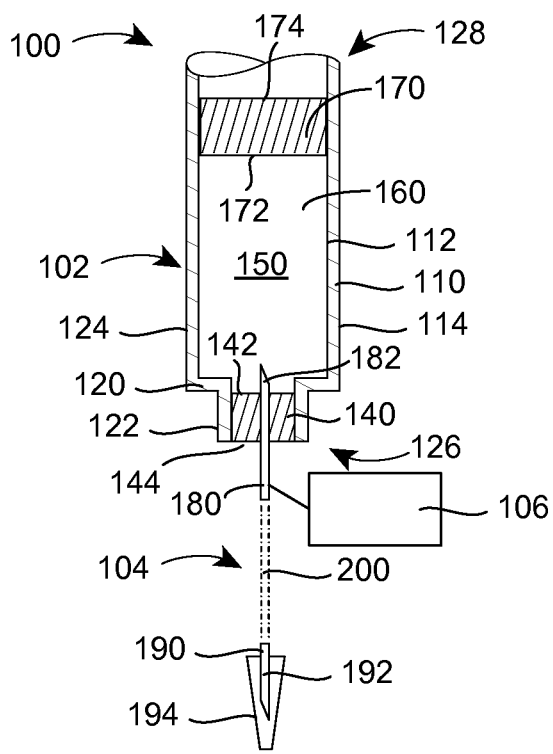
FIG. 3 is a cross-sectional view of the injector of FIG. 1, with the container needle in a delivery state wherein the needle penetrates the unitary wall of the container such that it is disposed through an interior surface of the flexible wall into a sterile reservoir.

The embodiment of the injector 100 illustrated in FIGS. 1 and 3 is exemplary. FIGS. 5 and 6 illustrate variants of the injector illustrated in FIGS. 1 and 3.

According to the embodiment of FIG. 5, the injector 300 includes a container 302, a fluid delivery device 304, and an actuator 306. Similar to the embodiment of FIGS. 1 and 3, the container 302 includes a wall 310 with interior and exterior surfaces 312, 314. The wall 310 may have two opposed ends 320, 322 with the interior surface 312 of the wall 310 defining a bore 324 between the opposing ends 320, 322.

Unlike the container 102, the container 302 has a fixed plug 326 that closes the end 320. In addition, while the container 302 has a flexible unitary wall 330 with interior and exterior surfaces 332, 334, the wall 330 is disposed within the end 322 of the container 302, and thus performs the role of the stopper/piston 170 in the container 102. Consequently, the wall 330 is moveable along the bore 324 between the opposing ends 320, 322. The interior surfaces 312, 332 of the walls 310, 330 define a sterile reservoir 340 in which a medical fluid or drug product 350 is disposed.

The fluid delivery device 304 may include a sterile container needle 360 having a point 362. The point 362 of the needle 360, like the point 182 of the needle 180, is disposed only partially into the flexible wall 330 in a storage state, with the actuator 306 causing the point 362 to move between the storage state and a delivery state wherein the point 362 is disposed through the interior surface 332 of the flexible wall 330 into the sterile reservoir 340. The container needle 360 may be in fluid communication with a injection needle 370 having a point 372 covered with a shield 374 through a cannula 380 received within a piston rod 382, for example, which rod 382 may be used to move the stopper/piston 330 between the ends 320, 322 of the container 302.

According to the embodiment illustrated in FIG. 6, a container has a wall 390 with interior and exterior surfaces 392, 394. Unlike the containers discussed previously, the wall 390 defines a closed end 396 and an open end 398. The container also includes a flexible wall 400, like the wall 330 of the embodiment of FIG. 5, which wall 400 is moveable within the container between the open end 398 and the closed end 396. According to this embodiment, a separate structure is not required to close off one of the ends 396, 398 because the wall 390 defines the closed end 396 itself. The closed end 396 may be resized so that it is radially larger than illustrated in FIG. 6.

Having discussed a plurality of embodiments wherein a seal assembly includes only a flexible unitary wall, a further plurality of embodiments will be discussed with reference to FIGS. 7-11 wherein the seal assembly includes a plurality of walls and/or seals. This structure may be referred to as a compartmentalized seal (or septum with reference to FIG. 7, or stopper with reference to FIGS. 8-11). While these walls and/or seals may be illustrated and referred to as a wall and a barrier, it will be recognized that these structures may be defined as part of a single structure (e.g., a single septum with a space formed in the center).

Figure 7:
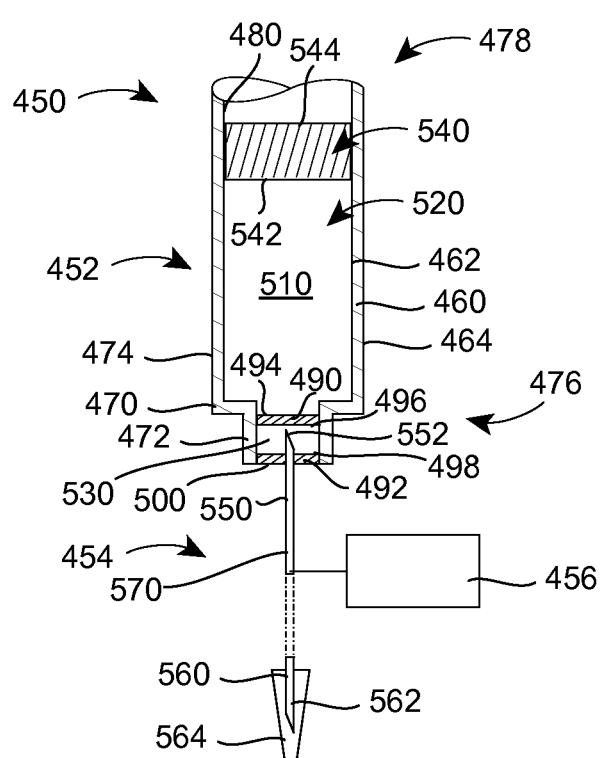
FIG. 7 is a cross-sectional view of an embodiment of an injector according to the present disclosure, with a container needle in a storage state wherein the needle partially penetrates a barrier, but not a flexible wall, of a seal assembly.

Referring to FIG. 7, an injector 450 includes a container 452, a fluid delivery system 454, and an actuator 456.

The container 452 includes a wall 460 with an interior surface 462 and an exterior surface 464. Similar to the container of FIGS. 1 and 2, the wall 460 may have a generally cylindrical shape, with a shoulder 470 separating a first cylindrical section 472 having a first cross-sectional diameter from a second cylindrical section 474 having a second cross-sectional diameter, the first cross-sectional diameter being smaller than the second cross-sectional diameter. The wall 460 may also define two opposed, open ends 476, 478. The wall 460, or more particularly, the interior surface 462 of the wall 460, may also define a bore 480.

Unlike the container 102 of FIGS. 1 and 3, the container 452 of FIG. 7 has a seal assembly that includes more than a single, unitary wall. The seal assembly of the container 452 includes a flexible wall 490 and a barrier 492. The flexible wall 490 has an interior surface 494 and an exterior surface 496, while the barrier 492 has an interior surface 498 and an exterior surface 500. The interior surfaces 462, 494 of the wall 460 and the flexible wall 490 define a closed sterile reservoir 510 to be filled with a medical fluid or drug product 520. In some embodiments, the barrier 492 is disposed exterior of the flexible wall 490 to define an enclosed space 530 between the flexible wall 490 and the barrier 492. The space 530 may be defined by the interior surface 462 of the wall 460, the exterior surface 496 of the flexible wall 490, and the interior surface 498 of the barrier 492.

The container 452 may also include a stopper or piston 540 with interior and exterior surfaces 542, 544. The piston 540 may be received within the end 478 defined by the wall 460, and may be moveable along the bore 480 between the ends 476, 478 of the container 452. According to such an embodiment, the reservoir 510 within which the medical fluid or drug product 520 is disposed may be defined by the interior surfaces 462, 494, 542 of the walls 460, 490 and piston 540.

The embodiment of FIG. 7 also includes the fluid delivery system 454 comprising a sterile container needle 550 having a point 552 disposed through the barrier 492 into the space 530 in a storage state, and disposed through the interior surface 494 of the flexible wall 490 into the sterile reservoir 510 in a delivery state. The container needle 550 only partially penetrates the seal assembly. The fluid delivery system 454 may also include an injection needle 560 with a point 562 covered at least initially with a needle shield 564 to prevent contact with and contamination of the point 562. The container needle 550 and the injection needle 560 may be connected by a cannula or tube 570, which may be a flexible cannula according to certain embodiments of the present disclosure.

Figure 8:
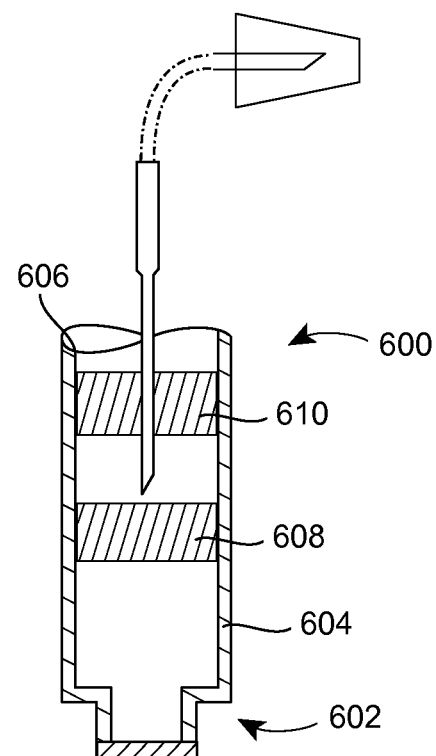
FIG. 8 is a cross-sectional view of an embodiment of an injector according to the present disclosure, with a container needle in a storage state wherein the needle partially penetrates a barrier, but not a flexible wall, of a seal assembly.

As shown in FIG. 8, the seal assembly of an injector 600 is disposed in a container 602 in place of the stopper/piston 540 illustrated relative to the container 452. That is, the container 602 includes a wall 604 that defines a bore 606, and a flexible wall 608 and a barrier 610 each define a stopper that is moveable along the bore 606. While the wall 604 of the container 602 does not define opposing open and closed ends in the embodiment illustrated, such an alternative is possible.

Figure 9:
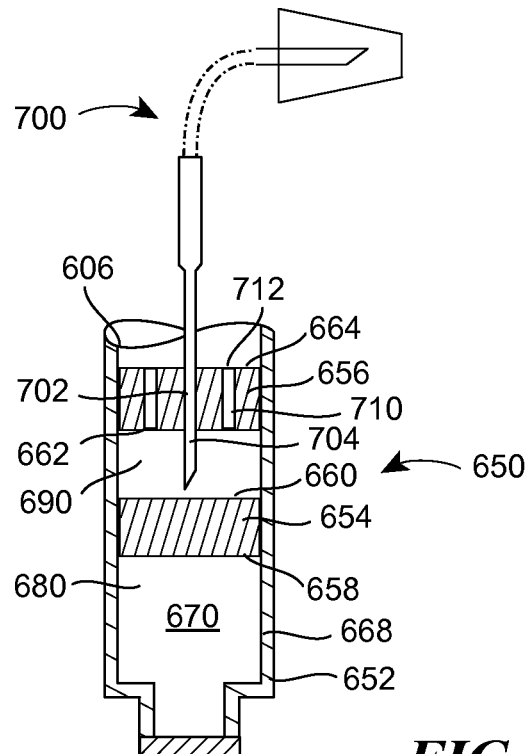
FIG. 9 is a cross-sectional view of an embodiment of an injector according to the present disclosure, including vents to evacuate a space between a flexible wall and an exteriorly disposed barrier as an associated container needle is moved between a storage state and a delivery state.
Figure 10:
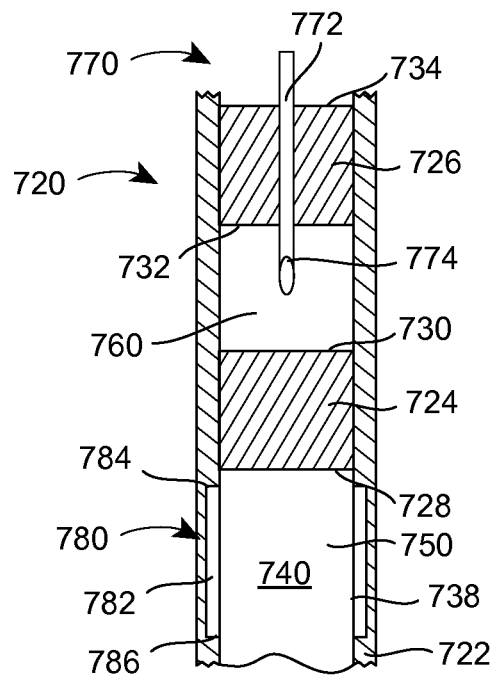
FIG. 10 is a cross-sectional view of an embodiment of an injector according to the present disclosure, including bypasses to evacuate a space between a flexible wall and an exteriorly disposed barrier as an associated container needle is moved between a storage state and a delivery state.
Figure 11:
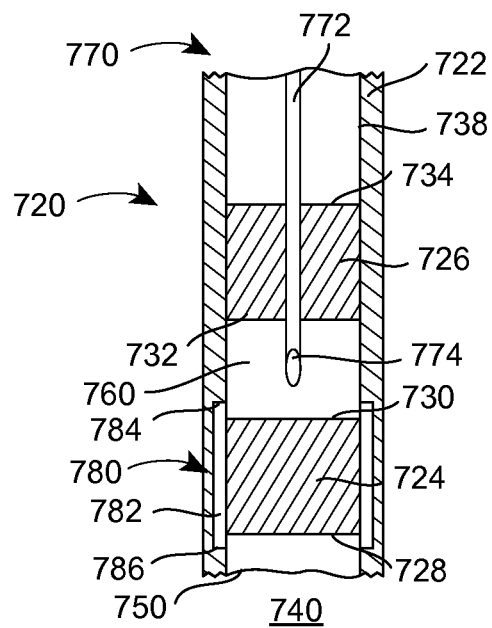
FIG. 11 is a cross-sectional view of the container of FIG. 10 in an intermediate state with the bypasses in fluid communication with a space defined between a flexible wall and a barrier.

FIGS. 9-11 illustrate variants to the embodiment illustrated in FIG. 8, which variants include additional features to permit the space or region between the flexible wall and the barrier to be evacuated or exhausted. These additional features may be referred to as vents, valves or bypasses, but all of these structures permit gases to escape from the space or region between the flexible wall and the barrier when an actuator moves the associated container needle from a storage state to a delivery state. This is not to suggest that the inner wall and exterior barrier cannot remain separated, for example through the use of a spacer or spacers, according to other embodiments of the present disclosure. The embodiments shown in FIGS. 9-11 illustrate options for evacuating the space where the inner wall and exterior barrier come together. It would be understood that the vents, valves, and bypasses would preserve a sterile condition within the space until the space is evacuated or exhausted.

A container 650 is illustrated in FIG. 9 including a wall 652 and a seal assembly, the assembly including a flexible wall 654 and a barrier 656. The flexible wall 654 has an interior surface 658 and an exterior surface 660, while the barrier 654 has an interior surface 662 and an exterior surface 664. An interior surface 668 of the wall 652 and the interior surface 658 of the flexible wall 654 define a closed sterile reservoir 670 to be filled with a medical fluid or drug product 680. The barrier 656 is disposed exterior of the flexible wall 654 to define an enclosed space 690 between the flexible wall 654 and the barrier 656. The space 690 may be defined by the interior surface 668 of the wall 652, the exterior surface 660 of the flexible wall 652, and the interior surface 662 of the barrier 656.

As illustrated in FIG. 10, a fluid delivery system 700 including a container needle 702 is used in conjunction with the seal assembly. The container needle 702 is shown in the storage state. The container needle 702 is disposed through the barrier 656 so that a point 704 of the needle 702 is disposed in the space 690. The point 704 will penetrate the flexible wall 654 and depend into the reservoir 670 in a delivery state (not shown). The needle 702 is not drawn to scale particularly as to its length.

The container 650 illustrated in FIG. 9 includes at least one vent 710. The vents 710 are in fluid communication with the space 690 between the barrier 656 and the flexible wall 654. The vents 710 are selectively actuated to permit gas trapped between the barrier 656 and the flexible wall 654 to escape through the vents 710 when the seal assembly is moved between the illustrated storage state and the delivery state, wherein the barrier 656 is advanced in the direction of the flexible wall 654 to permit the point 704 of the container needle 702 to penetrate through the wall 654. In some embodiments, the vents 710 may be in a sealed condition relative to the environment until actuated, for example, by a change in the pressure within the space 690.

The vents 710 are disposed within the barrier 656, and extend between the interior surface 662 and the exterior surface 664 of the barrier 656. A flap 712 covers the end of the vent 710 proximate to the exterior surface 664, and thereby seals the end of the vent 710 until the vent is actuated, preserving the sterility of the space 690 between the barrier 656 and the flexible wall 654. Alternatively, the vents 710 may be arranged, for example, in the wall 652 of the container 650.

FIGS. 10 and 11 illustrate a further variant on the system of FIG. 8, wherein a container 720 includes a wall 722 and a seal assembly, the assembly including a flexible wall 724 and a barrier 726. The flexible wall 724 has an interior surface 728 and an exterior surface 730, while the barrier 726 has an interior surface 732 and an exterior surface 734. An interior surface 738 of the wall 722 and the interior surface 728 of the flexible wall 724 define a closed sterile reservoir 740 to be filled with a medical fluid or drug product 750. The barrier 726 is disposed exterior of the flexible wall 724 to define an enclosed space 760 between the flexible wall 724 and the barrier 726. The space 760 may be defined by the interior surface 738 of the wall 722, the exterior surface 730 of the flexible wall 722, and the interior surface 732 of the barrier 726.

As illustrated in FIG. 10, a fluid delivery system 770 including a container needle 772 is used in conjunction with the seal assembly. The container needle 772 is illustrated in the storage state, wherein the container needle 772 is disposed through the barrier 726 so that a point 774 of the needle 772 is disposed in the space 760. The point 774 will penetrate the flexible wall 724 and depend into the reservoir 740 in a delivery state, not shown.

In contrast with the previously discussed embodiments, the container 720 illustrated in FIG. 10 includes at least one bypass or vent 780. The bypasses 780 are in fluid communication with the reservoir 740. The bypasses 780 are selectively actuated to permit gas trapped between the barrier 726 and the flexible wall 724 to escape through the bypasses 780 into the reservoir 740 when the seal assembly is moved between the illustrated storage state and the delivery state, wherein the barrier 726 is advanced in the direction of the flexible wall 724 to permit the point 774 of the container needle 772 to penetrate through the wall 724.

The bypasses 780 are not in fluid communication with the space 760 until the flexible wall 724 has moved from the storage state illustrated in FIG. 10 to an intermediate state illustrated in FIG. 11. As illustrated in FIGS. 10 and 11, the bypasses 780 may be defined in the interior surface 738 of the wall 722, and may take the form of a groove 782 formed in the wall 722. The groove 782 may have a distal end 784 and a proximal end 786. As will be recognized, until the exterior surface 730 of the flexible wall 724 moves past the distal end 784 of the grooves 782, the reservoir 740 is in a sealed condition relative to the space 760. However, once the exterior surface 730 of the flexible wall 724 moves past distal end 784 of the grooves 782, the gases trapped between the barrier 726 and the flexible wall 724 may exhaust into the reservoir 740. This may facilitate the movement of the barrier 726 and needle 770 toward the flexible wall 724.

Other embodiments of the present disclosure include embodiments where the container needle is not disposed through the seal assembly, or where the container needle is disposed fully through the seal assembly. Two such alternatives are illustrated in FIGS. 12 and 13.

FIGS. 12 and 13 illustrate embodiments wherein the container needle is disposed through the flexible wall (defining the stopper or septum) and a valve is used to seal the reservoir off from the injection needle. The valve may also be used to control the flow of medical fluid or drug product from the reservoir in the container. In this fashion, the valve may be used to meter an amount of medical fluid or drug product from the reservoir, or to delay the flow of the medical fluid or drug product until a time delay has elapsed relative to receipt of an input from an input device (e.g., button or switch), for example.

FIG. 12 illustrates an injector 850 with a container 852, a fluid delivery system 854, and an actuator 856. The container 852 includes a flexible wall 860, which may be in the form of a septum. The flexible wall 860 has an interior surface 862 and an exterior surface 864. Additionally, the fluid delivery system 854 includes a container needle 866, an injection needle 868, and a flexible cannula or tubing 870 connecting the container needle 866 and the injection needle 868. The injection needle 868 may be received within a cover 872 that preserves the sterility of the needle 868.

The container needle 866 (and in particular a point 874 of the container needle 866) is disposed through the flexible wall 860 and through the interior surface 862. The needle 866 is thus in fluid communication with a sterile reservoir 880 and a medical fluid or drug product 890 disposed within the reservoir 880. Fluid communication between the container needle 866 and the injection needle 868 is interrupted by valve 900 disposed in or along the flexible tubing 870. Unlike the other embodiments discussed above relative to FIGS. 1-11, the actuator 856 of the injector 850 is not used to move the container needle 866 relative to the flexible wall 860, but instead to manipulate the valve between a closed state wherein fluid communication is interrupted between the needles 866, 868 and an open state wherein the container needle 866 is in fluid communication with the injection needle 868.

The valve 900 may take a variety of shapes and forms, two of which are illustrated in FIGS. 12 and 13. In particular, FIG. 12 illustrates an embodiment of the injector 850 wherein a rotatable valve 900 is disposed in the flexible tubing 870, or has an internal valve member that is in fluid communication with the fluid flow path defined between the container needle 866 and the injection needle 868. FIG. 13 illustrates an embodiment of the injector wherein a pinch valve 902 is disposed along the flexible tubing 870, and thus cooperates with an exterior surface of the tubing 870 to interrupt the fluid communication between the container needle 866 and the injection needle 868.

Embodiments such as those illustrated in FIGS. 12 and 13 could also be used with a container that has a permanently attached needle, such that the container is in the form of a syringe, for example. In addition, the method described relative to FIG. 4 could be used with any of the embodiments mentioned heretofore, as well as with an embodiment like those illustrated in FIGS. 12 and 13 wherein no valve is used, but the syringe (i.e., a container with permanently attached needle) has an injection needle that is covered by a shield to maintain its sterility.

The embodiments illustrated in FIGS. 12 and 13 may be further modified to incorporate a seal assembly including a plurality of walls and/or seals, such as is illustrated in FIG. 7, for example. FIG. 14 illustrates such an embodiment.

In particular, FIG. 14 illustrates an injector 920 with a container 922, a fluid delivery system 924, an actuator 926, and a seal assembly 928. The fluid delivery system 924 may include a container needle 930, an injection needle 932, and a flexible cannula or tubing 934 connecting the container needle 930 and the injection needle 932. The injection needle 932 may be received within a cover 936 that preserves the sterility of the needle 932. The needle 932 may also be in selective fluid communication with a sterile reservoir 940 and a medical fluid or drug product 942 disposed within the reservoir 940 via a valve 944 disposed in or along the flexible tubing 934. In this regard, the injector 920 is similar to those injector embodiments illustrated in FIGS. 12 and 13.

However, the seal assembly 928 of the injector 920 also has a flexible wall 950 and a barrier 952. The flexible wall 950 and the barrier 952 each have interior and exterior surfaces, with the interior surface of the flexible wall 950 defining, in part, the closed sterile reservoir 940. The barrier 952 is disposed exterior of the flexible wall 950 to define an enclosed space 954 between the flexible wall 950 and the barrier 952 in which a point 956 of the container needle 930 may be disposed.

The embodiment of FIG. 14 has two potential barriers: one in the form of the valve 944 and a second in the form of the placement of the point 956 within the space 954. In some embodiments, the valve 944 may be controlled to provide a delay in the injection of the medical fluid or drug product 942 after the container needle 930 has been caused to penetrate trough the flexible wall 950 into the reservoir 940.

The devices according to the present disclosure may have one or more advantages relative to conventional technology, any one or more of which may be present in a particular embodiment in accordance with the features of the present disclosure included in that embodiment. As one example, these embodiments maintain the sterility of the medical fluid or drug product until the time of use. As another example, the potential for mixing of the medical fluid or drug product is limited or eliminated prior to the time of use. As a still further example, unintended delivery of the medical fluid or drug product is limited or prevented prior to the time of use.

Figure 15:
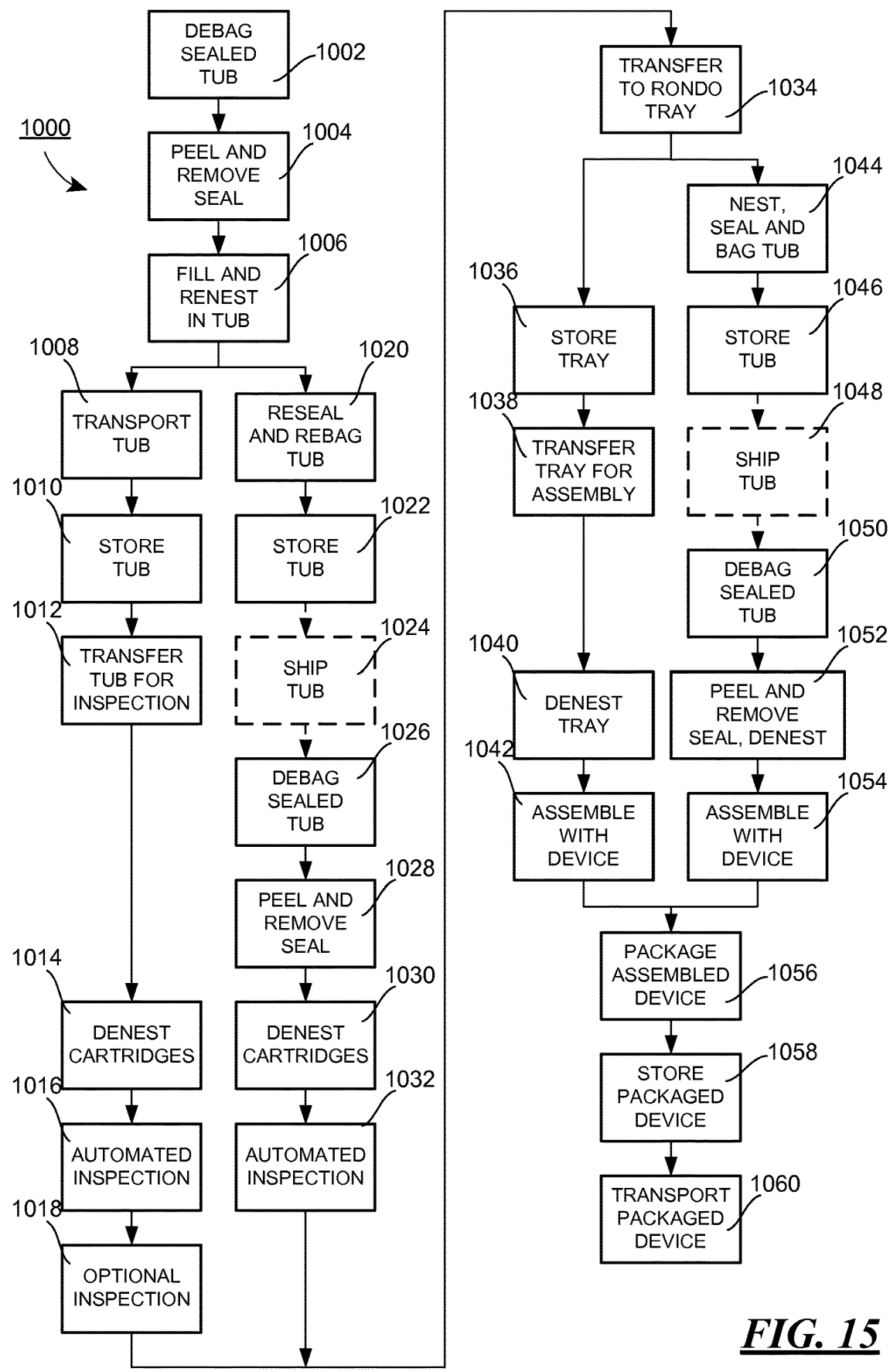
FIG. 15 is a flowchart illustrating a method of assembling an injector according to the present disclosure.

For illustrative purposes only, FIG. 15 provides a further method 1000 for assembling delivery devices according to any of the embodiments disclosed above. The method 1000 follows the general processing flow outlined above relative to FIG. 4. However, rather than referring to the cleanroom classifications according to U.S. Federal Standard 209E, reference is made to cleanroom classifications according to the GMP EU standard. Moreover, the method 1000 provides additional optional paths (represented as a left or right branch) that may be followed in the assembly of the delivery device. Consequently, the method 1000 of FIG. 15 may be viewed as supplementary to the discussion above relative to FIG. 4.

The method 1000 for assembling delivery devices begins at block 1002. The containers used in the device are initially stored in sealed tubs. These containers may be sterilized. At block 1002, the tubs are debagged, for example using an automated debagger in a Grade C cleanroom. At block 1004, the Tyvek seal is peeled off (e.g., by a robot) and removed, for example, in a space operated as a Grade A cleanroom, perhaps within an isolator in a space otherwise operated a Grade C cleanroom.

The containers are filled, and the stoppers and the fluid systems are attached, and then the containers are re-nested in open tubs, at block 1006, in a space operated as a Grade A cleanroom, perhaps within an isolator in a space otherwise operated a Grade C cleanroom. From this point, two different alternative paths, or branches, are possible.

The filled containers may be left in the open tubs at block 1008. The tubs may be conveyed and carted to a storage space (e.g., cold room) at block 1010.

If the route of block 1008, 1010 is followed, then the method 1000 may continue with the tubs being transferred for processing to an inspection room at block 1012. The filled containers are then denested from the open tubs at block 1014, and supplied to an automated inspection machine at block 1016. Automated inspection of the filled containers occurs at block 1016, followed by optional, additional semi-automated or manual inspection at block 1018.

Alternatively, the tubs may be resealed, rebagged, and labeled, at block 1020. For example, the tubs may be resealed with Tyvek (e.g., using a Bausch+Strobel tub sealer), rebagged, and then labeled in a Grade C cleanroom at block 1020. The tubs may then be stored, or even shipped, if necessary, at blocks 1022, 1024.

Once storage or transport is completed, the tubs are debagged, for example using an automated debagger at block 1026. At block 1028, the Tyvek seal is peeled off and removed. The filled containers may then be denested for inspection, at block 1030. The actions at blocks 1026, 1028, 1030 are performed in a Grade C cleanroom. An automated inspection may then be carried out using a visual inspection machine designed for operation in a Grade C cleanroom at block 1032.

Following either procedure, the filled, inspected containers may then be transferred to rondo trays at block 1034.

According to a first procedure, the rondo trays may be sent directly to storage at block 1036. If the route of block 1036 is followed, then the rondo trays are transferred for processing to the device assembly room at block 1038. The containers are denested at block 1040, and assembled with the other elements of the delivery device at block 1042 to define an assembled delivery device (e.g., an injector or an infuser).

Alternatively, the containers may be moved into tubs, which are sealed, bagged, and labeled, at block 1044. For example, the tubs may be resealed with Tyvek, bagged, and then labeled in a Grade C cleanroom. The tubs may then be stored, or even shipped for further processing, if necessary, at blocks 1046, 1048. Once storage or transport completed, the tubs are debagged, for example using an automated debagger at block 1050. At block 1052, the Tyvek seal is peeled off and removed, and the containers are denested. The filled containers may then be assembled with the other elements of the delivery device at block 1054. The actions at blocks 1050, 1052, 1054 may all occur in a Grade C cleanroom.

In either event, the assembled devices are packaged at block 1056, and the packaged, assembled devices are stored at block 1058. Finally, the packaged, assembled devices are transported to the distributor, and/or for other distribution actions at block 1060.

While numerous embodiments of an injector have been described above, still further embodiments are possible. FIGS. 16-22 and 24 illustrate a number of embodiments utilizing a mechanical connection or coupling between the container and the container needle. With reference to FIGS. 16-18, an injector 1100 according to such additional embodiments includes a container 1102, a seal assembly 1104 and a fluid delivery system 1106, which fluid delivery system 1106 includes a sterile container needle 1108. The fluid delivery system 1106 may include sterile flexible tubing connected at a first end to the container needle 1108 and a second end to a sterile injection needle received within a sterile cover that closes off the sterile injection needle, as discussed above. Unlike the embodiments described above, the sterile container needle 1108 is attached to a connector 1110, the connector 1110 being mechanically connected or coupled to the container 1102 to secure the sterile connector needle 1108 to the container 1102.

As illustrated in FIG. 16, the container 1102 may have a container wall 1120 with an interior surface 1122. In some embodiments, the container 1102 may include a rigid wall formed using, for example, any of the materials discussed above relative to the other containers discussed herein. The container 1102, and more particularly the container wall 1120, defines a bore 1124, and the container 1102 may include a stopper (or plunger) 1126 that is moveable along the bore 1124 between opposite ends 1128, 1130.

While the plunger 1126 closes one end 1130 of the container 1102, the other end 1128 of the container 1102 is closed by the seal assembly 1104. As illustrated, the seal assembly 1104 includes a flexible seal assembly wall 1140 and a barrier 1142.

The flexible seal assembly wall 1140 has an interior surface 1144, the interior surfaces 1122, 1144 of the container wall 1120 and the seal assembly wall 1140 defining a closed sterile reservoir 1146 that may be filled with a medical fluid or drug product. The container 1102 has an opening 1148 at the first end 1128 of the bore 1124, which opening 1148 is in fluid communication with the reservoir 1146, and the flexible seal assembly wall 1140 defines a septum disposed across the opening 1148. The flexible seal assembly wall 1140 is fixedly attached to the container wall 1120 as described in detail below relative to an exemplary embodiment.

The barrier 1142 is disposed exterior of the seal assembly wall 1140 (relative to the reservoir 1146) to define an enclosed space 1150 between the flexible wall 1140 and the barrier 1142. In particular, the barrier 1142 may have a cup-like shape defined by a plate 1152 with exterior and interior surfaces 1154, 1156 and a rim 1158 depending axially from the interior surface 1156 of the plate 1152. A surface 1160 of the rim 1158 is disposed on an exterior surface 1162 of the seal assembly wall 1140, the enclosed space 1150 being disposed between interior surface 1156 of the plate 1152, the exterior surface 1162 of the seal assembly wall 1140 and the rim 1158. In some embodiments, the barrier 1142 and the flexible seal assembly wall 1140 may be formed as a single structure with a space defined therebetween.

The fluid delivery system 1100 includes the sterile container needle 1108. This needle 1108 has a point 1170 that is disposed only through the barrier 1142 in a storage state (see FIG. 17), and that is disposed through the flexible wall 1140 into the sterile reservoir 1146 in a delivery state (see FIG. 18). As mentioned above, the sterile container needle 1108 is attached to a connector 1110 that is mechanically attached to the container 1102 to secure the sterile container needle 1108 to the container 1102 with the needle 1108 in the storage state. An actuator 1180 (see FIG. 16) is included that is itself adapted to move the container needle 1108 from the storage state to the delivery state, for example after receipt of a signal from a mechanical, electro-mechanical, or electrical input device coupled to the actuator 1180. According to certain embodiments, the actuator 1180 is adapted to delay movement of the container needle 1108 from the storage state to the delivery state to some predetermined time after an input is received.

The connector 1110 may be mechanically connected or coupled to the container 1102 using a variety of different mechanisms. For example, the connector may simply be press fit onto the container. FIG. 19 illustrates such an embodiment of the connector, which connector is formed of a cup-shaped collar 1190 through which the sterile container needle 1108 depends. The collar 1190 has a plate 1192 with exterior and interior surfaces 1194, 1196, and a rim 1198 depending axially from the interior surface 1196 of the plate 1192. The end of the container would be received within a space 1200 defined by the interior surface 1196 of the plate 1192 and the rim 1198, and an inner surface 1202 of the rim 1198 would frictionally engage the container to limit or prevent separation.

Alternatively, the connector 1110 may be a first connector of a pair of connectors, and a second connector 1210 of the pair of connectors may be attached to the container 1102. See, e.g., FIGS. 16-18. The first and second connectors 1110, 1210 may be mechanically coupled to secure the sterile container needle 1108 to the container 1102 in the storage state as illustrated in FIG. 17. For example, a family of connectors useful according embodiments of the disclosure may include first and second connectors each of which include one of a pair of facing surfaces. The facing surfaces abut to limit movement of the first and second connectors axially along a longitudinal axis of the sterile container needle, and thus limit or prevent separation of the sterile container needle from the container and the seal assembly.

FIGS. 16-18 and 20 illustrate an embodiment of such a connector pair. According to this embodiment, the first and second connectors 1110, 1210 engage to rotatably couple the pair of connectors 1110, 1210 to secure the sterile container needle 1108 to the container 1102 in the storage state. That is, the illustrated first and second connectors 1110, 1210 limit or prevent separation of the sterile connector needle 1108 from the container 1102 in the axial direction, but do not work to limit or prevent the needle 1108 and associated connector 1110 from rotating relative to the container/seal assembly 1102/1104.

As seen in FIG. 20, the connector includes a cup-shaped collar 1220 through which the sterile container needle 1108 depends. The collar 1220 has a plate 1222 with exterior and interior surfaces 1224, 1226, and a rim 1228 depending axially from the interior surface 1126 of the plate 1222. The rim 1228 defines an opening 1230 through which an end of the container 1102 is disposed when the sterile container needle 1108 is secured to the container 1102. Disposed about the opening 1230 is an inwardly directed flange 1232 that defines one surface 1234 of a pair of facing surfaces, an outwardly directed flange 1236 attached to the container 1102 defining the other surface 1238. See also FIGS. 16 and 17. The abutment of the facing surfaces 1234, 1238 limits or prevents separation once the needle 1108 and connector 1110 have been advanced in the direction of the container 1102 such that the flange 1232 is moved axially past the flange 1236 in the direction of the container 1102.

According to the embodiment illustrated in FIGS. 16, 17, and 19, the container 1102 comprises a rim 1240 disposed about the opening 1148. The seal assembly 1104 is disposed over the opening 1148 of the container 1102, with a portion of the seal assembly wall 1140 disposed through the opening 1148. The second connector 1210 includes an outwardly-directed flange 1246 that defines a rim, at least the portion of the second connector 1210 defined by the rim 1246 disposed over the seal assembly 1104. The container 1102 further includes a crimp ring 1250, the ring 1250 being formed about the rim 1240 of the container 1102 and the rim 1246 of the second connector 1210 with the seal assembly 1104 disposed between the rims 1240, 1246 to secure the seal assembly 1104 between the rim 1240 of the container 1102 and the rim 1246 of the second connector 1210.

According to this embodiment, the second connector 1210 also has an passage 1252 therethrough. The sterile container needle 1108 is disposed through the passage 1252 in the second connector 1210 and through the barrier 1142 in the storage state, and through the passage 1252, the barrier 1142 and the seal assembly wall 1140 in the delivery state. Of course, such an embodiment has been included by way of illustration, and not by way of limitation.

To assemble the device illustrated in FIGS. 16-18, the container needle 1108 and the connector 1110 is advanced in the direction of the container 1102. As the needle 1108 passes through the barrier 1142, the inwardly-directed flange 1232 of the connector 1110 moves past the outwardly directed flange 1236 of the connector 1210 attached to the container 1102. Once the flange 1232 has moved past the flange 1236, the movement of the container needle 1108 and the associated connector 1110 is prevented by abutting surfaces 1234, 1238. The material selected for the flange 1232 and/or the flange 1236 may be selected to resist a significant force applied to the container needle 1108 and the connector 1110 to separate the needle 1108 from the container 1102. The material is also selected, however, to permit the flanges 1232, 1236 to move past each other so that the mechanical coupling can be formed, and/or the collar 1220 of the connector 1110 may have features (e.g., axial slots) that permit the collar 1220 or sections of the collar 1220 to flex to permit the motion of the flange 1232 past the flange 1236.

FIG. 21 illustrates a connector that may be used with a different embodiment of the connector pair. According to this embodiment, the first and second connectors of the connector pair would threadingly engage to couple the connector pair to secure the sterile container needle to the container in the storage state. Accordingly, relative rotational motion between the first and second connector would cause the connectors to either be securely coupled to each other or to decouple from each other, and thus relative rotational motion is to be limited (unlike the embodiment of FIGS. 16-18 and 20, wherein relative rotation motion is permitted). As illustrated in FIG. 21, the first connector of such a connector paid may have a collar 1260 with a plate 1262 having exterior and interior surfaces 1264, 1266, and a rim 1268 depending axially from the interior surface 1266 of the plate 1262. The rim 1268 defines an opening 1270 through which an end of the container is disposed when the sterile container needle is secured to the container. On an inner surface of the rim 1268, a thread 1272 is formed, which thread 1272 would be matched with a mating thread formed on the second connector.

As illustrated in FIGS. 16-21, the first connector of a connector pair may include a collar that is disposed continuously about the sterile connector needle. Alternatively, as illustrated in FIG. 22, the first connector may include a collar that is disposed discontinuously about the sterile connector needle. According to the embodiment illustrated in FIG. 22, the connector includes a collar 1280 that is significantly discontinuous, to the point where the collar 1280 defines only a pair of arms 1282 disposed opposite from each other relative to the container needle 1108 that is disposed between the two arms 1282. The arms 1282 are connected to a plate 1284 having exterior and interior surfaces 1286, 1288. Because of the relatively limited width of the arms 1282, the arms 1282 may have an end 1290 that is attached to the plate 1284 and that defines a living hinge, permitting the arms 1282 to pivot relative to the plate 1284 and the end 1290. The arms 1282 may also have an inwardly-directed flange or finger 1292 that will mate with a corresponding structure of the container, such as the flange 1236 of the container 1102 illustrated in FIGS. 16 and 17, to limit or prevent axial motion between the container 1102 and the needle 1108 such that the container needle 1108 would separate from the container 1102.

Figure 23:
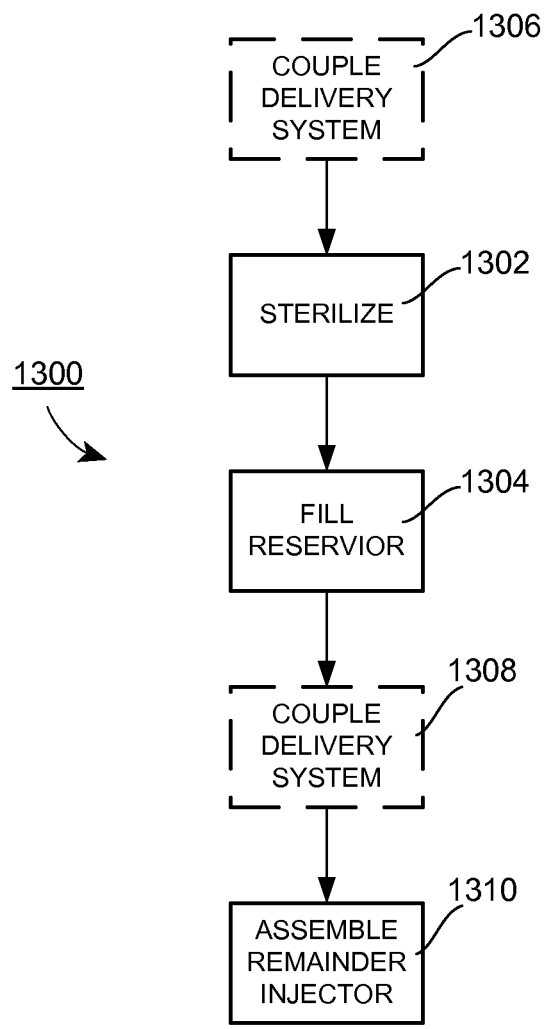
FIG. 23 is a flowchart illustrating a method of assembling an injector according to the present disclosure.

Accordingly, a method 1300 of assembling an injector, such as the injector 1100 illustrated in FIGS. 16-18 and 19, is illustrated in FIG. 23. The method 1300 may include sterilizing a reservoir 1146 at block 1302 and filling a sterile reservoir 1146 of a container 1102 with a medical fluid or drug product under sterile conditions at block 1304, the reservoir 1146 defined by an interior surface 1122 of a wall 1120 of the container 1102. A sterile fluid delivery system 1106 (e.g., the container needle 1108) may be mechanically connected or coupled to the container 1102 under sterile conditions, the fluid delivery system 1106 not in fluid communication with the reservoir 1146 in a storage state and in fluid communication with the reservoir 1146 in a delivery state, and assembling the remainder of the injector 1100 under clean room conditions. In particular, the steps of sterilizing and filling the sterile reservoir 1146 may follow the step of mechanically connecting or coupling the sterile fluid delivery system 1106 to the container 1102, as illustrated at block 1306. According to other embodiments, the step of mechanically connecting or coupling the sterile fluid delivery system 1106 to the container 1102 may follow the step of filling the sterile reservoir 1146, as illustrated at block 1308. The step of mechanically connecting or coupling the sterile fluid delivery system 1106 may occur within a fill/finish suite, for example. Assembly of the remainder of the injector 1100 may also include attaching the fluid delivery system 1106 to an actuator 1180 under clean room conditions at block 1310, the actuator 1180 adapted to change the state of the fluid delivery system 1106 from the storage state to a delivery state.

The connection of the needle to the container (and specifically to the flexible seal assembly wall/barrier) prior to the sterilization and filing of the container is not limited to the embodiments of FIGS. 16-22. It will be recognized that the method 1000 described in regard to the FIG. 15 may be performed in accordance with the method described in FIG. 23. In particular, rather than assembling the container needle with the reservoir at block 1006 of the method 1000 of FIG. 15, the container needle (and associated tubing/delivery needle) may be assembled with the reservoir even prior to block 1002, such that the container needle/container assembly may be filled and renested in the tub at block 1006. The method 1000 may then continue as described above.

It will also be recognized that while the embodiments of FIGS. 16-22 have been described relative to a system wherein a combination of a seal wall and a barrier is provided, a similar system with mechanical connection or coupling of the container needle and container may be provided utilizing any of the embodiments described in FIGS. 1-14. To illustrate this point, an additional embodiment according to the present disclosure is provided in FIG. 24 with an injector 1330 including a container 1332, a seal assembly 1334 and a fluid delivery system 1336, which fluid delivery system 1336 includes a sterile container needle 1338. The fluid delivery system 1336 may include sterile flexible tubing connected at a first end to the container needle 1338 and a second end to a sterile injection needle received within a sterile cover that closes off the sterile injection needle, as discussed above. The sterile container needle 1338 is attached to a connector 1340, the connector 1340 being mechanically connected or coupled to the container 1332 to secure the sterile connector needle 1338 to the container 1332.

The container 1332 may have a container wall 1342 with an interior surface 1344, and a stopper (or plunger) 1346 that is moveable between opposite ends 1348, 1350. While the plunger 1346 closes one end 1350 of the container 1332, the other end 1348 of the container 1332 is closed by the seal assembly 1334. As illustrated, the seal assembly 1334 includes a flexible seal assembly wall 1352.

The flexible seal assembly wall 1352 has an interior surface 1354, the interior surfaces 1344, 1354 of the container wall 1342 and the seal assembly wall 1352 defining a closed sterile reservoir 1356. The container 1332 has an opening 1358 at the first end 1348 in fluid communication with the reservoir 1356, and the flexible seal assembly wall 1352 defines a septum disposed across the opening 1358. The needle 1338 has a point 1360 that is disposed only partially through the wall 1352 in a storage state, as illustrated in FIG. 24, and that is disposed through the flexible wall 1352 into the sterile reservoir 1356 in a delivery state.

As mentioned above, the sterile container needle 1338 is attached to a connector 1340 that is mechanically attached to the container 1332 to secure the sterile container needle 1338 to the container 1332 with the needle 1338 in the storage state. In particular, a second connector 1362 is connected to the container 1332. The connector 1340 has an inwardly directed flange 1364 that defines one surface 1366 of a pair of facing surfaces, an outwardly directed flange 1368 attached to the container 1332 defining the other surface 1370. The abutment of the facing surfaces 1366, 1370 limits or prevents separation once the needle 1338 and connector 1340 have been advanced in the direction of the container 1332 such that the flange 1364 is moved axially past the flange 1368 in the direction of the container 1332 Advantages and embodiments not specifically listed herein may also be recognized For example, while the operation of the actuator has been described with regard to the foregoing embodiments as moving, the container needle from a storage state to a delivery state, it will be understood that the actuator may also move the container needle from the delivery state to the storage state. If a dose of medical fluid or drug product is to be delivered that is less than the volume of the reservoir (such as may be the case wherein the injector is designed to be programmed to deliver an adjustable dose according to the needs of the patient (e.g., pediatric vs. adult patient)), then the actuator may move the container needle from the storage state to the delivery state prior to delivery of the dose, and from the delivery state to the storage state after delivery of the dose. The movement from the delivery state to the storage state will in effect reseal the container and close the fluid path to the patient. This sequence of movement between the storage state and the delivery state may be repeated. As noted above, maintaining a closed fluid path until delivery is initiated is advantageous in that the opportunity for unintended delivery of the medical fluid or drug product to the patient and/or mixing of the medical fluid or drug product with the patient's bodily fluids is reduced.

The injectors according to the present disclosure may be used with a variety of medical fluids or drug products, including colony stimulating factors, such as granulocyte colouny-stimulating factor (G-CSF). Such G-CSF agents include, but are not limited to, Neupogen® (filgrastim) and Neulasta® (pegfilgrastim). In various other embodiments, the drug delivery device may be used with various pharmaceutical products, such as an erythropoiesis stimulating agent (ESA), which may be in a liquid or a lyophilized form. An ESA is any molecule that stimulates erythropoiesis, such as Epogen® (epoetin alfa), Aranesp® (darbepoetin alfa), Dynepo® (epoetin delta), Mircera® (methoxy polyethylene glycol-epoetin beta), Hematide®, MRK-2578, INS-22, Retacrit® (epoetin zeta), Neorecormon® (epoetin beta), Silapo® (epoetin zeta), Binocrit® (epoetin alfa), epoetin alfa Hexal, Abseamed® (epoetin alfa), Ratioepo® (epoetin theta), Eporatio® (epoetin theta), Biopoin® (epoetin theta), epoetin alfa, epoetin beta, epoetin zeta, epoetin theta, and epoetin delta, as well as the molecules or variants or analogs thereof as disclosed in the following patents or patent applications, each of which is herein incorporated by reference in its entirety: U.S. Pat. Nos. 4,703,008; 5,441,868; 5,547,933; 5,618,698; 5,621,080; 5,756,349; 5,767,078; 5,773,569; 5,955,422; 5,986,047; 6,583,272; 7,084,245; and 7,271,689; and PCT Publ. Nos. WO 91/05867; WO 95/05465; WO 96/40772; WO 00/24893; WO 01/81405; and WO 2007/136752.

An ESA can be an erythropoiesis stimulating protein. As used herein, "erythropoiesis stimulating protein" means any protein that directly or indirectly causes activation of the erythropoietin receptor, for example, by binding to and causing dimerization of the receptor. Erythropoiesis stimulating proteins include erythropoietin and variants, analogs, or derivatives thereof that bind to and activate erythropoietin receptor; antibodies that bind to erythropoietin receptor and activate the receptor; or peptides that bind to and activate erythropoietin receptor. Erythropoiesis stimulating proteins include, but are not limited to, epoetin alfa, epoetin beta, epoetin delta, epoetin omega, epoetin iota, epoetin zeta, and analogs thereof, pegylated erythropoietin, carbamylated erythropoietin, mimetic peptides (including EMP1/hematide), and mimetic antibodies. Exemplary erythropoiesis stimulating proteins include erythropoietin, darbepoetin, erythropoietin agonist variants, and peptides or antibodies that bind and activate erythropoietin receptor (and include compounds reported in U.S. Publ. Nos. 2003/0215444 and 2006/0040858, the disclosures of each of which is incorporated herein by reference in its entirety) as well as erythropoietin molecules or variants or analogs thereof as disclosed in the following patents or patent applications, which are each herein incorporated by reference in its entirety: U.S. Pat. Nos. 4,703,008; 5,441,868; 5,547,933; 5,618,698; 5,621,080; 5,756,349; 5,767,078; 5,773,569; 5,955,422; 5,830,851; 5,856,298; 5,986,047; 6,030,086; 6,310,078; 6,391,633; 6,583,272; 6,586,398; 6,900,292; 6,750,369; 7,030,226; 7,084,245; and 7,217,689; US Publ. Nos. 2002/0155998; 2003/0077753; 2003/0082749; 2003/0143202; 2004/0009902; 2004/0071694; 2004/0091961; 2004/0143857; 2004/0157293; 2004/0175379; 2004/0175824; 2004/0229318; 2004/0248815; 2004/0266690; 2005/0019914; 2005/0026834; 2005/0096461; 2005/0107297; 2005/0107591; 2005/0124045; 2005/0124564; 2005/0137329; 2005/0142642; 2005/0143292; 2005/0153879; 2005/0158822; 2005/0158832; 2005/0170457; 2005/0181359; 2005/0181482; 2005/0192211; 2005/0202538; 2005/0227289; 2005/0244409; 2006/0088906; and 2006/0111279; and PCT Publ. Nos. WO 91/05867; WO 95/05465; WO 99/66054; WO 00/24893; WO 01/81405; WO 00/61637; WO 01/36489; WO 02/014356; WO 02/19963; WO 02/20034; WO 02/49673; WO 02/085940; WO 03/029291; WO 2003/055526; WO 2003/084477; WO 2003/094858; WO 2004/002417; WO 2004/002424; WO 2004/009627; WO 2004/024761; WO 2004/033651; WO 2004/035603; WO 2004/043382; WO 2004/101600; WO 2004/101606; WO 2004/101611; WO 2004/106373; WO 2004/018667; WO 2005/001025; WO 2005/001136; WO 2005/021579; WO 2005/025606; WO 2005/032460; WO 2005/051327; WO 2005/063808; WO 2005/063809; WO 2005/070451; WO 2005/081687; WO 2005/084711; WO 2005/103076; WO 2005/100403; WO 2005/092369; WO 2006/50959; WO 2006/02646; and WO 2006/29094.

Examples of other pharmaceutical products for use with the device may include, but are not limited to, antibodies such as Vectibix® (panitumumab), Xgeva™ (denosumab) and Prolia™ (denosamab); other biological agents such as Enbrel® (etanercept, TNF-receptor/Fc fusion protein, TNF blocker), Neulasta® (pegfilgrastim, pegylated filgastrim, pegylated G-CSF, pegylated hu-Met-G-CSF), Neupogen® (filgrastim, G-CSF, hu-MetG-CSF), and Nplate® (romiplostim); small molecule drugs such as Sensipar® (cinacalcet). The device may also be used with a therapeutic antibody, a polypeptide, a protein or other chemical, such as an iron, for example, ferumoxytol, iron dextrans, ferric glyconate, and iron sucrose. The pharmaceutical product may be in liquid form, or reconstituted from lyophilized form.

Among particular illustrative proteins are the specific proteins set forth below, including fusions, fragments, analogs, variants or derivatives thereof:

OPGL specific antibodies, peptibodies, and related proteins, and the like (also referred to as RANKL specific antibodies, peptibodies and the like), including fully humanized and human OPGL specific antibodies, particularly fully humanized monoclonal antibodies, including but not limited to the antibodies described in PCT Publ. No. WO 03/002713, which is incorporated herein in its entirety as to OPGL specific antibodies and antibody related proteins, particularly those having the sequences set forth therein, particularly, but not limited to, those denoted therein: 9H7; 18B2; 2D8; 2E11; 16E1; and 22B3, including the OPGL specific antibodies having either the light chain of SEQ ID NO: 2 as set forth therein in FIG. 2 and/or the heavy chain of SEQ ID NO:4, as set forth therein in FIG. 4, each of which is individually and specifically incorporated by reference herein in its entirety fully as disclosed in the foregoing Publication;

Myostatin binding proteins, peptibodies, and related proteins, and the like, including myostatin specific peptibodies, particularly those described in US Publ. No. 2004/0181033 and PCT Publ. No. WO 2004/058988, which are incorporated by reference herein in their entirety particularly in parts pertinent to myostatin specific peptibodies, including but not limited to peptibodies of the mTN8-19 family, including those of SEQ ID NOS: 305-351, including TN8-19-1 through TN8-19-40, TN8-19 con1 and TN8-19 con2; peptibodies of the mL2 family of SEQ ID NOS: 357-383; the mL15 family of SEQ ID NOS: 384-409; the mL17 family of SEQ ID NOS: 410-438; the mL20 family of SEQ ID NOS: 439-446; the mL21 family of SEQ ID NOS: 447-452; the mL24 family of SEQ ID NOS: 453-454; and those of SEQ ID NOS: 615-631, each of which is individually and specifically incorporated by reference herein in their entirety fully as disclosed in the foregoing publication;

IL-4 receptor specific antibodies, peptibodies, and related proteins, and the like, particularly those that inhibit activities mediated by binding of IL-4 and/or IL-13 to the receptor, including those described in PCT Publ. No. WO 2005/047331 or PCT Appl. No. PCT/US2004/37242 and in US Publ. No. 2005/112694, which are incorporated herein by reference in their entirety particularly in parts pertinent to IL-4 receptor specific antibodies, particularly such antibodies as are described therein, particularly, and without limitation, those designated therein: L1H1; L1H2; L1H3; L1H4; L1H5; L1H6; L1H7; L1H8; L1H9; L1H10; L1H11; L2H1; L2H2; L2H3; L2H4; L2H5; L2H6; L2H7; L2H8; L2H9; L2H10; L2H11; L2H12; L2H13; L2H14; L3H1; L4H1; L5H1; L6H1, each of which is individually and specifically incorporated by reference herein in its entirety fully as disclosed in the foregoing publication;

Interleukin 1-receptor 1 ("IL1-R1") specific antibodies, peptibodies, and related proteins, and the like, including but not limited to those described in U.S. Publ. No. 2004/097712A1, which is incorporated herein by reference in its entirety in parts pertinent to IL1-R1 specific binding proteins, monoclonal antibodies in particular, especially, without limitation, those designated therein: 15CA, 26F5, 27F2, 24E12, and 10H7, each of which is individually and specifically incorporated by reference herein in its entirety fully as disclosed in the aforementioned U.S. publication;

Ang2 specific antibodies, peptibodies, and related proteins, and the like, including but not limited to those described in PCT Publ. No. WO 03/057134 and U.S. Publ No. 2003/0229023, each of which is incorporated herein by reference in its entirety particularly in parts pertinent to Ang2 specific antibodies and peptibodies and the like, especially those of sequences described therein and including but not limited to: L1(N); L1(N) WT; L1(N) 1K WT; 2×L1(N); 2×L1(N) WT; Con4 (N), Con4 (N) 1K WT, 2×Con4 (N) 1K; L1C; L1C1K; 2×L1C; Con4C; Con4C1K; 2×Con4C1K; Con4-L1 (N); Con4-L1C; TN-12-9 (N); C17 (N); TN8-8(N); TN8-14 (N); Con 1 (N), also including anti-Ang 2 antibodies and formulations such as those described in PCT Publ. No. WO 2003/030833 which is incorporated herein by reference in its entirety as to the same, particularly Ab526; Ab528; Ab531; Ab533; Ab535; Ab536; Ab537; Ab540; Ab543; Ab544; Ab545; Ab546; A551; Ab553; Ab555; Ab558; Ab559; Ab565; AbF1AbFD; AbFE; AbFJ; AbFK; AbG1D4; AbGC1E8; AbH1C12; AblAl; AblF; AblK, AblP; and AblP, in their various permutations as described therein, each of which is individually and specifically incorporated by reference herein in its entirety fully as disclosed in the foregoing publication;

NGF specific antibodies, peptibodies, and related proteins, and the like including, in particular, but not limited to those described in US Publ. No. 2005/0074821 and U.S. Pat. No. 6,919,426, which are incorporated herein by reference in their entirety particularly as to NGF-specific antibodies and related proteins in this regard, including in particular, but not limited to, the NGF-specific antibodies therein designated 4D4, 4G6, 6H9, 7H2, 14D10 and 14D11, each of which is individually and specifically incorporated by reference herein in its entirety fully as disclosed in the foregoing publication;

CD22 specific antibodies, peptibodies, and related proteins, and the like, such as those described in U.S. Pat. No. 5,789,554, which is incorporated herein by reference in its entirety as to CD22 specific antibodies and related proteins, particularly human CD22 specific antibodies, such as but not limited to humanized and fully human antibodies, including but not limited to humanized and fully human monoclonal antibodies, particularly including but not limited to human CD22 specific IgG antibodies, such as, for instance, a dimer of a human-mouse monoclonal hLL2 gamma-chain disulfide linked to a human-mouse monoclonal hLL2 kappa-chain, including, but limited to, for example, the human CD22 specific fully humanized antibody in Epratuzumab, CAS registry number 501423-23-0;

IGF-1 receptor specific antibodies, peptibodies, and related proteins, and the like, such as those described in PCT Publ. No. WO 06/069202, which is incorporated herein by reference in its entirety as to IGF-1 receptor specific antibodies and related proteins, including but not limited to the IGF-1 specific antibodies therein designated L1H1, L2H2, L3H3, L4H4, L5H5, L6H6, L7H7, L8H8, L9H9, L10H10, L11H11, L12H12, L13H13, L14H14, L15H15, L16H16, L17H17, L18H18, L19H19, L20H20, L21H21, L22H22, L23H23, L24H24, L25H25, L26H26, L27H27, L28H28, L29H29, L30H30, L31H31, L32H32, L33H33, L34H34, L35H35, L36H36, L37H37, L38H38, L39H39, L40H40, L41H41, L42H42, L43H43, L44H44, L45H45, L46H46, L47H47, L48H48, L49H49, L50H50, L51H51, L52H52, and IGF-1R-binding fragments and derivatives thereof, each of which is individually and specifically incorporated by reference herein in its entirety fully as disclosed in the foregoing International Publication;

Also among non-limiting examples of anti-IGF-1R antibodies for use in the methods and compositions of the present invention are each and all of those described in:

(i) US Publ. No. 2006/0040358 (published Feb. 23, 2006), 2005/0008642 (published Jan. 13, 2005), 2004/0228859 (published Nov. 18, 2004), including but not limited to, for instance, antibody 1A (DSMZ Deposit No. DSM ACC 2586), antibody 8 (DSMZ Deposit No. DSM ACC 2589), antibody 23 (DSMZ Deposit No. DSM ACC 2588) and antibody 18 as described therein;

(ii) PCT Publ. No. WO 06/138729 (published Dec. 28, 2006) and WO 05/016970 (published Feb. 24, 2005), and Lu et al., 2004, J Biol. Chem. 279:2856-65, including but not limited to antibodies 2F8, A12, and IMC-A12 as described therein;

(iii) PCT Publ. No. WO 07/012614 (published Feb. 1, 2007), WO 07/000328 (published Jan. 4, 2007), WO 06/013472 (published Feb. 9, 2006), WO 05/058967 (published Jun. 30, 2005), and WO 03/059951 (published Jul. 24, 2003);

(iv) US Publ. No. 2005/0084906 (published Apr. 21, 2005), including but not limited to antibody 7C10 chimaeric antibody C7C10, antibody h7C10, antibody 7H2M, chimaeric antibody *7C10, antibody GM 607, humanized antibody 7C10 version 1, humanized antibody 7C10 version 2, humanized antibody 7C10 version 3, and antibody 7H2HM, as described therein;

(v) US Publ. Nos. 2005/0249728 (published Nov. 10, 2005), 2005/0186203 (published Aug. 25, 2005), 2004/0265307 (published Dec. 30, 2004), and 2003/0235582 (published Dec. 25, 2003) and Maloney et al., 2003, Cancer Res. 63:5073-83, including but not limited to antibody EM164, resurfaced EM164, humanized EM164, huEM164 v1.0, huEM164 v1.1, huEM164 v1.2, and huEM164 v1.3 as described therein;

(vi) U.S. Pat. No. 7,037,498 (issued May 2, 2006), US Publ. Nos. 2005/0244408 (published Nov. 30, 2005) and 2004/0086503 (published May 6, 2004), and Cohen, et al., 2005, Clinical Cancer Res. 11:2063-73, e.g., antibody CP-751,871, including but not limited to each of the antibodies produced by the hybridomas having the ATCC accession numbers PTA-2792, PTA-2788, PTA-2790, PTA-2791, PTA-2789, PTA-2793, and antibodies 2.12.1, 2.13.2, 2.14.3, 3.1.1, 4.9.2, and 4.17.3, as described therein;

(vii) US Publ. Nos. 2005/0136063 (published Jun. 23, 2005) and 2004/0018191 (published Jan. 29, 2004), including but not limited to antibody 19D12 and an antibody comprising a heavy chain encoded by a polynucleotide in plasmid 15H12/19D12 HCA (γ4), deposited at the ATCC under number PTA-5214, and a light chain encoded by a polynucleotide in plasmid 15H12/19D12 LCF (κ), deposited at the ATCC under number PTA-5220, as described therein; and (viii) US Publ. No. 2004/0202655 (published Oct. 14, 2004), including but not limited to antibodies PINT-6A1, PINT-7A2, PINT-7A4, PINT-7A5, PINT-7A6, PINT-8A1, PINT-9A2, PINT-11A1, PINT-11A2, PINT-11A3, PINT-11A4, PINT-11A5, PINT-11A7, PINT-11A12, PINT-12A1, PINT-12A2, PINT-12A3, PINT-12A4, and PINT-12A5, as described therein; each and all of which are herein incorporated by reference in their entireties, particularly as to the aforementioned antibodies, peptibodies, and related proteins and the like that target IGF-1 receptors;

B-7 related protein 1 specific antibodies, peptibodies, related proteins and the like ("B7RP-1," also is referred to in the literature as B7H2, ICOSL, B7h, and CD275), particularly B7RP-specific fully human monoclonal IgG2 antibodies, particularly fully human IgG2 monoclonal antibody that binds an epitope in the first immunoglobulin-like domain of B7RP-1, especially those that inhibit the interaction of B7RP-1 with its natural receptor, ICOS, on activated T cells in particular, especially, in all of the foregoing regards, those disclosed in U.S. Publ. No. 2008/0166352 and PCT Publ. No. WO 07/011941, which are incorporated herein by reference in their entireties as to such antibodies and related proteins, including but not limited to antibodies designated therein as follow: 16H (having light chain variable and heavy chain variable sequences SEQ ID NO:1 and SEQ ID NO:7 respectively therein); 5D (having light chain variable and heavy chain variable sequences SEQ ID NO:2 and SEQ ID NO:9 respectively therein); 2H (having light chain variable and heavy chain variable sequences SEQ ID NO:3 and SEQ ID NO:10 respectively therein); 43H (having light chain variable and heavy chain variable sequences SEQ ID NO:6 and SEQ ID NO:14 respectively therein); 41H (having light chain variable and heavy chain variable sequences SEQ ID NO:5 and SEQ ID NO:13 respectively therein); and 15H (having light chain variable and heavy chain variable sequences SEQ ID NO:4 and SEQ ID NO:12 respectively therein), each of which is individually and specifically incorporated by reference herein in its entirety fully as disclosed in the foregoing US. Publication;

IL-15 specific antibodies, peptibodies, and related proteins, and the like, such as, in particular, humanized monoclonal antibodies, particularly antibodies such as those disclosed in U.S. Publ. Nos. 2003/0138421; 2003/023586; and 2004/0071702; and U.S. Pat. No. 7,153,507, each of which is incorporated herein by reference in its entirety as to IL-15 specific antibodies and related proteins, including peptibodies, including particularly, for instance, but not limited to, HuMax IL-15 antibodies and related proteins, such as, for instance, 146B7;

IFN gamma specific antibodies, peptibodies, and related proteins and the like, especially human IFN gamma specific antibodies, particularly fully human anti-IFN gamma antibodies, such as, for instance, those described in US Publ. No. 2005/0004353, which is incorporated herein by reference in its entirety as to IFN gamma specific antibodies, particularly, for example, the antibodies therein designated 1118; 1118*; 1119; 1121; and 1121*. The entire sequences of the heavy and light chains of each of these antibodies, as well as the sequences of their heavy and light chain variable regions and complementarity determining regions, are each individually and specifically incorporated by reference herein in its entirety fully as disclosed in the foregoing US Publication and in Thakur et al., Mol. Immunol. 36:1107-1115 (1999). In addition, description of the properties of these antibodies provided in the foregoing US publication is also incorporated by reference herein in its entirety. Specific antibodies include those having the heavy chain of SEQ ID NO: 17 and the light chain of SEQ ID NO:18; those having the heavy chain variable region of SEQ ID NO:6 and the light chain variable region of SEQ ID NO:8; those having the heavy chain of SEQ ID NO:19 and the light chain of SEQ ID NO:20; those having the heavy chain variable region of SEQ ID NO:10 and the light chain variable region of SEQ ID NO:12; those having the heavy chain of SEQ ID NO:32 and the light chain of SEQ ID NO:20; those having the heavy chain variable region of SEQ ID NO:30 and the light chain variable region of SEQ ID NO:12; those having the heavy chain sequence of SEQ ID NO:21 and the light chain sequence of SEQ ID NO:22; those having the heavy chain variable region of SEQ ID NO:14 and the light chain variable region of SEQ ID NO:16; those having the heavy chain of SEQ ID NO:21 and the light chain of SEQ ID NO:33; and those having the heavy chain variable region of SEQ ID NO:14 and the light chain variable region of SEQ ID NO:31, as disclosed in the foregoing US Publication. A specific antibody contemplated is antibody 1119 as disclosed in foregoing US Publication and having a complete heavy chain of SEQ ID NO:17 as disclosed therein and having a complete light chain of SEQ ID NO:18 as disclosed therein;

TALL-1 specific antibodies, peptibodies, and the related proteins, and the like, and other TALL specific binding proteins, such as those described in U.S. Publ. Nos. 2003/0195156 and 2006/0135431, each of which is incorporated herein by reference in its entirety as to TALL-1 binding proteins, particularly the molecules of Tables 4 and 5B, each of which is individually and specifically incorporated by reference herein in its entirety fully as disclosed in the foregoing US Publications;

Parathyroid hormone ("PTH") specific antibodies, peptibodies, and related proteins, and the like, such as those described in U.S. Pat. No. 6,756,480, which is incorporated herein by reference in its entirety, particularly in parts pertinent to proteins that bind PTH;

Thrombopoietin receptor ("TPO-R") specific antibodies, peptibodies, and related proteins, and the like, such as those described in U.S. Pat. No. 6,835,809, which is herein incorporated by reference in its entirety, particularly in parts pertinent to proteins that bind TPO-R;

Hepatocyte growth factor ("HGF") specific antibodies, peptibodies, and related proteins, and the like, including those that target the HGF/SF:cMet axis (HGF/SF: c-Met), such as the fully human monoclonal antibodies that neutralize hepatocyte growth factor/scatter (HGF/ SF) described in US Publ. No. 2005/0118643 and PCT Publ. No. WO 2005/017107, huL2G7 described in U.S. Pat. No. 7,220,410 and OA-5d5 described in U.S. Pat. Nos. 5,686,292 and 6,468,529 and in PCT Publ. No. WO 96/38557, each of which is incorporated herein by reference in its entirety, particularly in parts pertinent to proteins that bind HGF;

TRAIL-R2 specific antibodies, peptibodies, related proteins and the like, such as those described in U.S. Pat. No. 7,521,048, which is herein incorporated by reference in its entirety, particularly in parts pertinent to proteins that bind TRAIL-R2;

Activin A specific antibodies, peptibodies, related proteins, and the like, including but not limited to those described in US Publ. No. 2009/0234106, which is herein incorporated by reference in its entirety, particularly in parts pertinent to proteins that bind Activin A;

TGF-beta specific antibodies, peptibodies, related proteins, and the like, including but not limited to those described in U.S. Pat. No. 6,803,453 and US Publ. No. 2007/0110747, each of which is herein incorporated by reference in its entirety, particularly in parts pertinent to proteins that bind TGF-beta;

Amyloid-beta protein specific antibodies, peptibodies, related proteins, and the like, including but not limited to those described in PCT Publ. No. WO 2006/081171, which is herein incorporated by reference in its entirety, particularly in parts pertinent to proteins that bind amyloid-beta proteins. One antibody contemplated is an antibody having a heavy chain variable region comprising SEQ ID NO: 8 and a light chain variable region having SEQ ID NO: 6 as disclosed in the International Publication;

c-Kit specific antibodies, peptibodies, related proteins, and the like, including but not limited to those described in Publ. No. 2007/0253951, which is incorporated herein by reference in its entirety, particularly in parts pertinent to proteins that bind c-Kit and/or other stem cell factor receptors;

OX40L specific antibodies, peptibodies, related proteins, and the like, including but not limited to those described in U.S. application Ser. No. 11/086,289, which is incorporated herein by reference in its entirety, particularly in parts pertinent to proteins that bind OX40L and/or other ligands of the OX40 receptor; and Other exemplary proteins, including Activase® (alteplase, tPA); Aranesp® (darbepoetin alfa); Epogen®

(epoetin alfa, or erythropoietin); GLP-1, Avonex® (interferon beta-1a); Bexxar® (tositumomab, anti-CD22 monoclonal antibody); Betaseron® (interferon-beta); Campath® (alemtuzumab, anti-CD52 monoclonal antibody); Dynepo® (epoetin delta); Velcade® (bortezomib); MLN0002 (anti-α4ß7 mAb); MLN1202 (anti-CCR2 chemokine receptor mAb); Enbrel® (etanercept, TNF-receptor/Fc fusion protein, TNF blocker); Eprex® (epoetin alfa); Erbitux® (cetuximab, anti-EGFR/HER1/c-ErbB-1); Genotropin® (somatropin, Human Growth Hormone); Herceptin® (trastuzumab, anti-HER2/neu (erbB2) receptor mAb); Humatrope® (somatropin, Human Growth Hormone); Humira® (adalimumab); insulin in solution; Infergen® (interferon alfacon-1); Natrecor® (nesiritide; recombinant human B-type natriuretic peptide (hBNP); Kineret® (anakinra); Leukine® (sargamostim, rhuGM-CSF); LymphoCide® (epratuzumab, anti-CD22 mAb); Benlysta™ (lymphostat B, belimumab, anti-BlyS mAb); Metalyse® (tenecteplase, t-PA analog); Mircera® (methoxy polyethylene glycol-epoetin beta); Mylotarg® (gemtuzumab ozogamicin); Raptiva® (efalizumab); Cimzia® (certolizumab pegol, CDP 870); Soliris™ (eculizumab); pexelizumab (anti-C5 complement); Numax® (MEDI-524); Lucentis® (ranibizumab); Panorex® (17-1A, edrecolomab); Trabio® (lerdelimumab); TheraCim hR3 (nimotuzumab); Omnitarg (pertuzumab, 2C4); Osidem® (IDM-1); OvaRex® (B43.13); Nuvion® (visilizumab); cantuzumab mertansine (huC242-DM1); NeoRecormon® (epoetin beta); Neumega® (oprelvekin, human interleukin-11); Neulasta® (pegylated filgastrim, pegylated G-CSF, pegylated hu-Met-G-CSF); Neupogen® (filgrastim, G-CSF, hu-MetG-CSF); Orthoclone OKT3® (muromonab-CD3, anti-CD3 monoclonal antibody); Procrit® (epoetin alfa); Remicade® (infliximab, anti-TNFα monoclonal antibody); Reopro® (abciximab, anti-GP IIb/Ilia receptor monoclonal antibody); Actemra® (anti-IL6 Receptor mAb); Avastin® (bevacizumab), HuMax-CD4 (zanolimumab); Rituxan® (rituximab, anti-CD20 mAb); Tarceva® (erlotinib); Roferon-A®-(interferon alfa-2a); Simulect® (basiliximab); Prexige® (lumiracoxib); Synagis® (palivizumab); 146B7-CHO (anti-IL15 antibody, see U.S. Pat. No. 7,153,507); Tysabri® (natalizumab, anti-α4integrin mAb); Valortim® (MDX-1303, anti-*B. anthracis* protective antigen mAb); ABthrax™; Vectibix® (panitumumab); Xolair® (omalizumab); ETI211 (anti-MRSA mAb); IL-1 trap (the Fc portion of human IgG1 and the extracellular domains of both IL-1 receptor components (the Type I receptor and receptor accessory protein)); VEGF trap (Ig domains of VEGFR1 fused to IgG1 Fc); Zenapax® (daclizumab); Zenapax® (daclizumab, anti-IL-2Ra mAb); Zevalin® (ibritumomab tiuxetan); Zetia® (ezetimibe); Orencia® (atacicept, TACI-Ig); anti-CD80 monoclonal antibody (galiximab); anti-CD23 mAb (lumiliximab); BR2-Fc (huBR3/huFc fusion protein, soluble BAFF antagonist); CNTO 148 (golimumab, anti-TNFα mAb); HGS-ETR1 (mapatumumab; human anti-TRAIL Receptor-1 mAb); HuMax-CD20 (ocrelizumab, anti-CD20 human mAb); HuMax-EGFR (zalutumumab); M200 (volociximab, anti-α5β1 integrin mAb); MDX-010 (ipilimumab, anti-CTLA-4 mAb and VEGFR-1 (IMC-18F1); anti-BR3 mAb; anti-*C. difficile* Toxin A and Toxin B C mAbs MDX-066 (CDA-1) and MDX-1388); anti-CD22 dsFv-PE38 conjugates (CAT-3888 and CAT-8015); anti-CD25 mAb (HuMax-TAC); anti-CD3 mAb (NI-0401); adecatumumab; anti-CD30 mAb (MDX-060); MDX-1333 (anti-IFNAR); anti-CD38 mAb (HuMax CD38); anti-CD40L mAb; anti-Cripto mAb; anti-CTGF Idiopathic Pulmonary Fibrosis Phase I Fibrogen (FG-3019); anti-CTLA4 mAb; anti-eotaxinl mAb (CAT-213); anti-FGF8 mAb; anti-ganglioside GD2 mAb; anti-ganglioside GM2 mAb; anti-GDF-8 human mAb (MYO-029); anti-GM-CSF Receptor mAb (CAM-3001); anti-HepC mAb (HuMax HepC); anti-IFNα mAb (MEDI-545, MDX-1103); anti-IGF1R mAb; anti-IGF-1R mAb (HuMax-Inflam); anti-IL12 mAb (ABT-874); anti-IL12/IL23 mAb (CNTO 1275); anti-IL13 mAb (CAT-354); anti-IL2Ra mAb (HuMax-TAC); anti-IL5 Receptor mAb; anti-integrin receptors mAb (MDX-018, CNTO 95); anti-IP10 Ulcerative Colitis mAb (MDX-1100); anti-LLY antibody; BMS-66513; anti-Mannose Receptor/hCGß mAb (MDX-1307); anti-mesothelin dsFv-PE38 conjugate (CAT-5001); anti-PD1mAb (MDX-1106 (ONO-4538)); anti-PDGFRα antibody (IMC-3G3); anti-TGFß mAb (GC-1008); anti-TRAIL Receptor-2 human mAb (HGS-ETR2); anti-TWEAK mAb; anti-VEGFR/Flt-1 mAb; anti-ZP3 mAb (HuMax-ZP3); NVS Antibody #1; and NVS Antibody #2.

Also included can be a sclerostin antibody, such as but not limited to romosozumab, blosozumab, or BPS 804 (Novartis). Further included can be therapeutics such as rilotumumab, bixalomer, trebananib, ganitumab, conatumumab, motesanib diphosphate, brodalumab, vidupiprant, panitumumab, denosumab, NPLATE, PROLIA, VECTIBIX or XGEVA. Additionally, included in the device can be a monoclonal antibody (IgG) that binds human Proprotein Convertase Subtilisin/Kexin Type 9 (PCSK9), e.g. U.S. Pat. No. 8,030,547, U.S. Ser. No. 13/469,032, WO2008/057457, WO2008/057458, WO2008/057459, WO2008/063382, WO2008/133647, WO2009/100297, WO2009/100318, WO2011/037791, WO2011/053759, WO2011/053783, WO2008/125623, WO2011/072263, WO2009/055783, WO2012/0544438, WO2010/029513, WO2011/111007, WO2010/077854, WO2012/088313, WO2012/101251, WO2012/101252, WO2012/101253, WO2012/109530, and WO2001/031007.

Also included can be talimogene laherparepvec or another oncolytic HSV for the treatment of melanoma or other cancers. Examples of oncolytic HSV include, but are not limited to talimogene laherparepvec (U.S. Pat. Nos. 7,223, 593 and 7,537,924); OncoVEXGALV/CD (U.S. Pat. No. 7,981,669); OrienX010 (Lei et al., 2013, World Journal of Gastroenterology, 19:5138-5143); G207, 1716; NV1020; NV12023; NV1034 and NV1042 (Vargehes et al. 2002, Cancer Gene Ther, 2002, 9 (12): 967-978).

Also included are TIMPs. TIMPs are endogenous tissue inhibitors of metalloproteinases (TIMPs) and are important in many natural process. TIMP-3 is expressed by various cells or and is present in the extracellular matrix; it inhibits all the major cartilage-degrading metalloproteases, and may play a role in role in many degradative diseases of connective tissue, including rheumatoid arthritis and osteoarthritis, as well as in cancer and cardiovascular conditions. The amino acid sequence of TIMP-3, and the nucleic acid sequence of a DNA that encodes TIMP-3, are disclosed in U.S. Pat. No. 6,562,596, issued May 13, 2003, the disclosure of which is incorporated by reference herein. Description of TIMP mutations can be found in U.S. 61/782,613, U.S. 61/798,160, U.S. 61/802,988, and U.S. 61/940,67.

Also included are antagonistic antibodies for human calcitonin gene-related peptide (CGRP) receptor and bispecific antibody molecule that target the CGRP receptor and other headache targets. Further information concerning these molecule can be found in WO2A075238A1.

Additionally, a bispecific T cell engager antibody (BiTe), e.g. Blinotumomab can be used in the device. Alternatively, included can be an APJ large molecule agonist e.g., apelin or analogues thereof in the device. Information relating to such molecules can be found in PCT/2013/075773, each of which (U.S. and PCT) is incorporated herein by reference in its entirety, particularly in parts pertinent to proteins that bind PCSK9.

I claim:

1. An injector comprising:
a container including a container wall with an interior surface, wherein the container wall defines a bore;
a seal assembly including a wall and a barrier, the wall fixedly attached to the container wall and the barrier having a cup-like shape defined by a plate and a rim, the rim disposed on the wall such that the plate is disposed exterior of the wall, the wall and barrier defining an enclosed space between the wall, the plate of the barrier, and the rim of the barrier;
a fluid delivery system comprising a container needle having a point disposed only through the barrier in a storage state such that the container needle is not in fluid communication with the bore, and disposed through the wall into the bore in a delivery state such that the container needle is in fluid communication with the bore, wherein only the container needle, the barrier, and the wall define the enclosed space in both the storage state and the delivery state;
the container needle attached to a connector, the connector mechanically coupled to the container to secure the container needle to the container with the container needle in the storage state; and
an electromechanical actuator coupled to the fluid delivery system and adapted to move the container needle from the storage state to the delivery state.

2. The injector of claim 1, wherein the container wall at least partially defines a reservoir.

3. The injector of claim 2, wherein the reservoir is filled with a medical fluid or drug product.

4. The injector of claim 3, wherein the medical fluid or drug product comprises a granulocyte colony-stimulating factor (G-CSF).

5. The injector of claim 4, wherein the G-CSF is pegylated.

6. The injector of claim 3, wherein the medical fluid or drug product comprises: an erythropoiesis stimulating agent; a TNF blocker; a interleukin-receptor specific antibody; an IGF-receptor (Insulin Growth Factor receptor) specific antibody; a TGF-specific antibody; or a PCSK9 (Proprotein Convertase Subtilisin/Kexin Type 9)-specific antibody.

7. The injector of claim 1, wherein the connector is press fit onto the container.

8. The injector of claim 1, wherein the connector is a first connector of a pair of connectors, a second connector of the pair of connectors being attached to the container, the first and second of the pair of connectors mechanically coupled to secure the container needle to the container in the storage state.

9. The injector of claim 8, wherein the first and second connectors each comprise one of a pair of facing surfaces, the facing surfaces abutting to limit movement of the first and second connectors axially along a longitudinal axis of the container needle.

10. The injector of claim 9, wherein the first and second connectors engage to rotatably couple the pair of connectors to secure the container needle to the container in the storage state.

11. The injector of claim 8, wherein the first connector comprises a collar disposed continuously or discontinuously about the container needle.

12. The injector of claim 1, wherein the container wall defines an opening at a first end of the bore, and the wall defines a septum disposed across the opening and fixedly attached to the container wall.

13. The injector of claim 1, wherein the fluid delivery system comprises sterile flexible tubing connected at a first end to the container needle and a second end to an injection needle.

14. The injector of claim 1, wherein the barrier and the wall are fixed relative to one another to define the enclosed space therebetween.

15. The injector of claim 1, wherein the barrier and wall of the seal assembly are formed as a single structure defining the enclosed space.

16. An injector comprising:
a container including a container wall with an interior surface, wherein the container wall defines a bore;
a seal assembly including a wall and a barrier, the wall fixedly attached to the container wall and the barrier having a cup-like shape defined by a plate and a rim, the rim disposed on the wall such that the plate is disposed exterior of the wall, the wall and barrier defining an enclosed space between the wall, the plate of the barrier, and the rim of the barrier;
a fluid delivery system comprising a container needle having a point disposed only through the barrier in a storage state such that the container needle is not in fluid communication with the bore, and disposed through the wall into the bore in a delivery state such that the container needle is in fluid communication with the bore, wherein the barrier and the wall define the enclosed space in both the storage state and the delivery state;
the container needle attached to a connector, the connector mechanically coupled to the container to secure the container needle to the container with the container needle in the storage state; and
an electromechanical actuator coupled to the fluid delivery system and adapted to move the container needle from the storage state to the delivery state,
wherein the connector is a first connector of a pair of connectors, a second connector of the pair of connectors being attached to the container, the first and second of the pair of connectors mechanically coupled to secure the container needle to the container in the storage state, and
wherein the container comprises a rim disposed about an opening, the seal assembly being disposed over the opening in the container, and the second connector comprising a rim and disposed over the seal assembly, the container further comprising a crimp ring formed about the rim of the container and the rim of the second connector with the seal assembly disposed between the rims to secure the seal assembly between the rim of the container and the rim of the second connector.

17. An injector comprising:
- a container including a container wall with an interior surface, wherein the container wall defines a bore;
- a seal assembly including a wall and a barrier, the wall fixedly attached to the container wall and the barrier having a cup-like shape defined by a plate and a rim, the rim disposed on the wall such that the plate is disposed exterior of the wall, the wall and barrier defining an enclosed space between the wall, the plate of the barrier, and the rim of the barrier;
- a fluid delivery system comprising a container needle having a point disposed only through the barrier in a storage state such that the container needle is not in fluid communication with the bore, and disposed through the wall into the bore in a delivery state such that the container needle is in fluid communication with the bore, wherein the barrier and the wall define the enclosed space in both the storage state and the delivery state;
- the container needle attached to a connector, the connector mechanically coupled to the container to secure the container needle to the container with the container needle in the storage state; and
- an electromechanical actuator coupled to the fluid delivery system and adapted to move the container needle from the storage state to the delivery state,
- wherein the connector is a first connector of a pair of connectors, a second connector of the pair of connectors being separate from and coupled with the container, the first and second of the pair of connectors being mechanically coupled to secure the container needle to the container with the container needle in the storage state, and
- wherein the second connector is disposed entirely forwardly of the container and spaced therefrom by the seal assembly.

18. The injector of claim 17, wherein the first and second connectors are movable with respect to one another to move the container needle to the delivery state.

* * * * *